US009958462B2

(12) United States Patent
Ramakrishnapillai et al.

(10) Patent No.: US 9,958,462 B2
(45) Date of Patent: *May 1, 2018

(54) ASSAY FOR DETECTION OF TRANSIENT INTRACELLULAR $CA^{2+}$

(71) Applicants: Rajiv Gandhi Centre for Biotechnology, Thiruvananthapuram (IN); Department of Biotechnology, New Delhi OT (IN)

(72) Inventors: Omkumar Vyomakesannair Ramakrishnapillai, Thiruvananthapuram (IN); Rajeev Kumar Raveendran, Thiruvananthapuram (IN); Mathew Steephan, Thiruvananthapuram (IN); Mayadevi Madhavan, Thiruvananthapuram (IN); Suma Priya Sudarsana Devi, Thiruvananthapuram (IN); Arunkumar Renganathan Chandrika, Thiruvananthapuram (IN); Archana Geetha Mohanan, Thiruvananthapuram (IN)

(73) Assignees: Rajiv Gandhi Centre for Biotechnology, Thiruvananthapuram (IN); Department of Biotechnology, New Delhi (IN)

( * ) Notice: Subject to any disclaimer, the term of this patent is extended or adjusted under 35 U.S.C. 154(b) by 0 days. days.

This patent is subject to a terminal disclaimer.

(21) Appl. No.: 13/661,787

(22) Filed: Oct. 26, 2012

(65) Prior Publication Data
US 2013/0089868 A1    Apr. 11, 2013

Related U.S. Application Data

(63) Continuation-in-part of application No. 12/665,599, filed as application No. PCT/IN2008/000370 on Jun. 12, 2008, now Pat. No. 8,304,198.

(30) Foreign Application Priority Data

Jun. 19, 2007 (IN) .............................. 1276/CHE/07

(51) Int. Cl.
C12N 5/10 (2006.01)
G01N 33/84 (2006.01)
G01N 33/68 (2006.01)
C07K 14/435 (2006.01)
C12N 9/12 (2006.01)
G01N 33/50 (2006.01)

(52) U.S. Cl.
CPC ....... *G01N 33/84* (2013.01); *C07K 14/43595* (2013.01); *C12N 9/12* (2013.01); *C12Y 207/11001* (2013.01); *G01N 33/5005* (2013.01); *G01N 33/6872* (2013.01); *C07K 2319/60* (2013.01); *G01N 2333/912* (2013.01)

(58) Field of Classification Search
None
See application file for complete search history.

(56) References Cited

U.S. PATENT DOCUMENTS

| 4,603,209 | A | 7/1986 | Tsien et al. |
| 5,049,673 | A | 9/1991 | Tsien et al. |
| 5,998,204 | A | 12/1999 | Tsien et al. |
| 6,469,154 | B1 | 10/2002 | Tsien et al. |
| 6,514,709 | B1 | 2/2003 | Grant et al. |

OTHER PUBLICATIONS

Bayer et al., "Transition from Reversible to Persistent Binding of CaMKII to Postsynaptic Sites and NR2B", The Journal of Neuroscience, Jan. 25, 2006, pp. 1164-1174, 26(4).
Caterina et al., "The capsaicin receptor: a heat-activated ion channel in the pain pathway", Nature, Oct. 23, 1997, pp. 816-824, vol. 389.
Cushing et al, "Measurement of calcium flux through ionotropic glutamate receptors using Cytostar-T scintillating microplates", Journal of Neuroscience Methods, 1999, pp. 33-36, 90.
Fujii et al., "Identification of Neuromedin U as the Cognate Ligand of the Orphan G Protein-coupled Receptor FM-3", The Journal of Biological Chemistry, Jul. 14, 2000, pp. 21068-21074, vol. 275, No. 28.
Grando et al., "Activation of Keratinocyte Nicotinic Cholinergic Receptors Stimulates Calcium Influx and Enhances Cell Differentiation", The Journal of Investigative Dermatology, 1996, pp. 412-418, vol. 107, No. 3, The Society for Investigative Dermatology, Inc.
Kunkel, "Rapid and Efficient Site-Specific Mutagenesis without Phenotypic Selection", Proceedings of the National Academy of Sciences of the United States of America, Jan. 15, 1985, pp. 488-492, vol. 82, No. 2.

(Continued)

Primary Examiner — Michael D Pak
(74) Attorney, Agent, or Firm — The Webb Law Firm

(57) ABSTRACT

This invention relates to a simple end point assay for detection of transient intracellular $Ca^{2+}$ with broad applicability to many $Ca^{2+}$ channel proteins comprising, Generation of expression constructs for the fusion proteins having the $Ca^{2+}$/calmodulin dependent protein kinase II (CaMKII) phosphorylation sites of NR2A or NR2B subunits of N-methyl-D-aspartate receptor (NMDAR) or the voltage gated potassium channel of *Drosophila* (Eag) or any protein sequence which binds to the T-site of CaMKII similar to NR2B, conjugated to mitochondrial localizing signal sequence, or mutants of these sequences as described herein. Generation of mammalian expression constructs of α-CaMKll as a chimera with green fluorescent protein (GFP-α-CaMKII) or its mutants as described herein. Site-Directed mutagenesis, Transfection, $Ca^{2+}$ stimulation, imaging and quantification of the number of cells with $Ca^{2+}$-dependent signal, wherein, NMDA receptor activity assay, TRPVl receptor activity assay, GluR4 receptor activity assay are performed to detect the activity of $Ca^{2+}$ channel proteins.

1 Claim, 22 Drawing Sheets

(56) References Cited

OTHER PUBLICATIONS

Mayadevi et al., "Sequence determinants on the NR2A and NR2B subunits of NMDA receptor responsible for specificity of phosphorylation by CaMKII", Biochimica et Biophysica Acta, 2002, pp. 40-45, 1598.

Omkumar et al., "Identification of a Phosphorylation Site for Calcium/Calmodulin-dependent Protein Kinase II in the NR2B Subunit of the N-Methyl-D-aspartate Receptor", The Journal of Biological Chemistry, Dec. 6, 1996, pp. 31670-31678, vol. 271, No. 49.

Praseeda et al., "Influence of a mutation in the ATP-binding region of Ca2+/calmodulin-dependent protein kinase II on its interaction with peptide substrates", Biochem J., 2004, pp. 391-397, 378.

Praseeda et al., "Interaction of peptide substrate outside the active site influences catalysis by CaMKII", Biochemical and Biophysical Research Communications, 2004, pp. 845-849, vol. 313.

Strack et al., "Mechanism and Regulation of Calcium/Calmodulin-dependent Protein Kinase II Targeting to the NR2B Subunit of the N-Methyl-D-aspartate Receptor", The Journal of Biological Chemistry, Aug. 4, 2000, pp. 23798-23806, vol. 275, No. 31.

Sun et al., "The eag Potassium Channel Binds and Locally Activates Calcium/Calmodulin-dependent Protein Kinase II", The Journal of Biological Chemistry, Mar. 12, 2004, pp. 10206-10214, vol. 279, No. 11.

Witte et al., "Use of a Fluorescent Imaging Plate Reader-Based Calcium Assay to Assess Pharmacological Differences between the Human and Rat Vanilloid Receptor", Journal of Biomolecular Screening, 2002, pp. 466-475, vol. 7, No. 5.

Scheme of the Ca²⁺-Sensing System

Ca$^{2+}$-Sensing System
(GFP-CaMKII and MLS-NR2B)

- Ca$^{2+}$ influx         + Ca$^{2+}$ influx

Confocal images

Nonconfocal image

Quantitation of $Ca^{2+}$-Dependent Signal

Image 1  Image 2

Increased Ca$^{2+}$-Dependent Signal produced by T286D mutant compared to wild-type α-CaMKII

Ca$^{2+}$-Sensing based on CaMKII-Eag Interaction

ASSAY FOR DETECTION OF TRANSIENT INTRACELLULAR CA$^{2+}$

This application is a continuation-in-part application of U.S. patent application Ser. No. 12/665,599, filed Jun. 9, 2010, now U.S. Pat. No. 8,304,198, which is the U.S. national phase of PCT Application No. PCT/IN08/00370, filed on Jun. 12, 2008, which claims priority to Indian Patent Application No. 1276/CHE/07, filed on Jun. 19, 2007, all of which are incorporated by reference herein in their entirety.

FIELD OF INVENTION

The invention relates to detection and quantification of transient changes in intracellular metabolites by making use of a resulting protein-protein interaction that is irreversible and longlasting.

BACKGROUND OF INVENTION

Increase in concentration of intracellular free Ca$^{2+}$ ions is a widely used signaling mechanism under various physiological conditions. Release of free Ca$^{2+}$ ions inside the cell happens either through plasma membrane channel proteins that allow Ca$^{2+}$ influx or by release from intracellular Ca$^{2+}$ stores. Since Ca$^{2+}$ release thus becomes the activity of a wide variety of proteins, methods for detection and measurement of intracellular free Ca$^{2+}$ are used as assays for many proteins that are potential drug targets. These methods should be capable of sensing the transient rise in intracellular [Ca$^{2+}$] and also of generating a detectable signal.

Most of the commonly used methods for Ca$^{2+}$ sensing use molecules that exhibit changes in their fluorescence characteristics upon exposure to increase in [Ca$^{2+}$]. These include small molecular weight macromolecules such as fura-2, indo-1, fluo-3, and Calcium-Green (U.S. Pat. Nos. 4,603,209 and 5,049,673) as well as proteins such as GFP (green fluorescent protein) family of proteins with a sensor peptide inserted within them (U.S. Pat. No. 6,469,154) or the cameleon molecules of tandem GFP constructs with an intervening Ca$^{2+}$ sensing peptide sequence, that generate a FRET signal upon sensing free Ca$^{2+}$ (U.S. Pat. No. 5,998,204). In all these methods, the fluorescence signal is also as short-lived as the Ca$^{2+}$-transient, and hence signal acquisition in real-time is mandatory. Moreover this also imposes rapid liquid dispensing. These factors not only necessitates the use of more expensive equipments but also limits the choice of equipments that can be used in addition to imposing severe constraints for carrying out these assays at high throughput scale. U.S. Pat. No. 6,514,709 disclosed a method that prolongs the duration of the Ca$^{2+}$-transients by incorporating an intracellular chelator that alters the kinetics of signal generation, so that the signal is prolonged. However in all these methods, measurements will have to be done on cells in the live condition.

OBJECTS OF THE INVENTION

The main object of this invention is to detect intracellular Ca$^{2+}$ transients using simple end point assay.

The other object is to develop a Ca$^{2+}$ sensing assay with broad applicability to many Ca$^{2+}$ channel proteins.

Another object is to detect intracellular Ca$^{2+}$ transients using a simple method wherein the need for realtime measurements on live cells is avoided.

STATEMENT OF INVENTION

This invention relates to a simple end point assay for detection of transient intracellular Ca$^{2+}$ with broad applicability to many Ca$^{2+}$ channel proteins comprising, Generation of expression constructs for the fusion proteins having the Ca$^{2+}$/calmodulin dependent protein kinase II (CaMKII) phosphorylation sites of NR2A or NR2B subunits of N-methyl-D-aspartate receptor (NMDAR) or the voltage gated potassium channel of Drosophila (Eag) or any protein sequence which binds to the T-site of CaMKII similar to NR2B, conjugated to mitochondrial localizing signal sequence, or mutants of these sequences as described herein. Generation of mammalian expression constructs of α-CaMKII as a chimera with green fluorescent protein (GFP-α-CaMKII) or its mutants as described herein. Site-Directed mutagenesis, Transfection, Ca$^{2+}$ stimulation, imaging and quantification of the number of cells with Ca$^{2+}$-dependent signal, wherein, NMDA receptor activity assay, TRPVI receptor activity assay, GluR4 receptor activity assay are performed to detect the activity of Ca$^{2+}$ channel proteins.

BRIEF DESCRIPTION OF THE ACCOMPANYING DRAWINGS

Figure 12A:
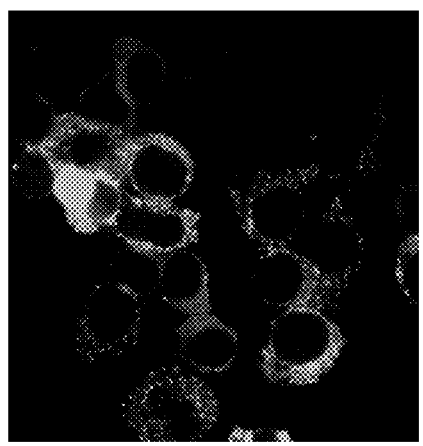
Figure 12B:
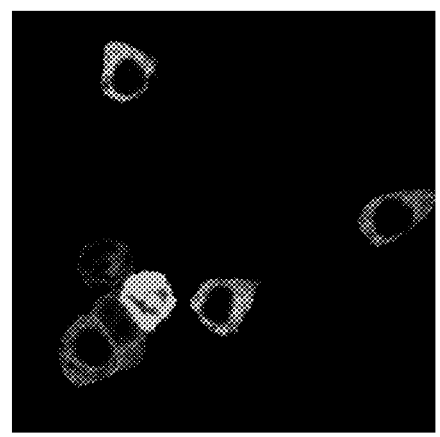
Figure 13:
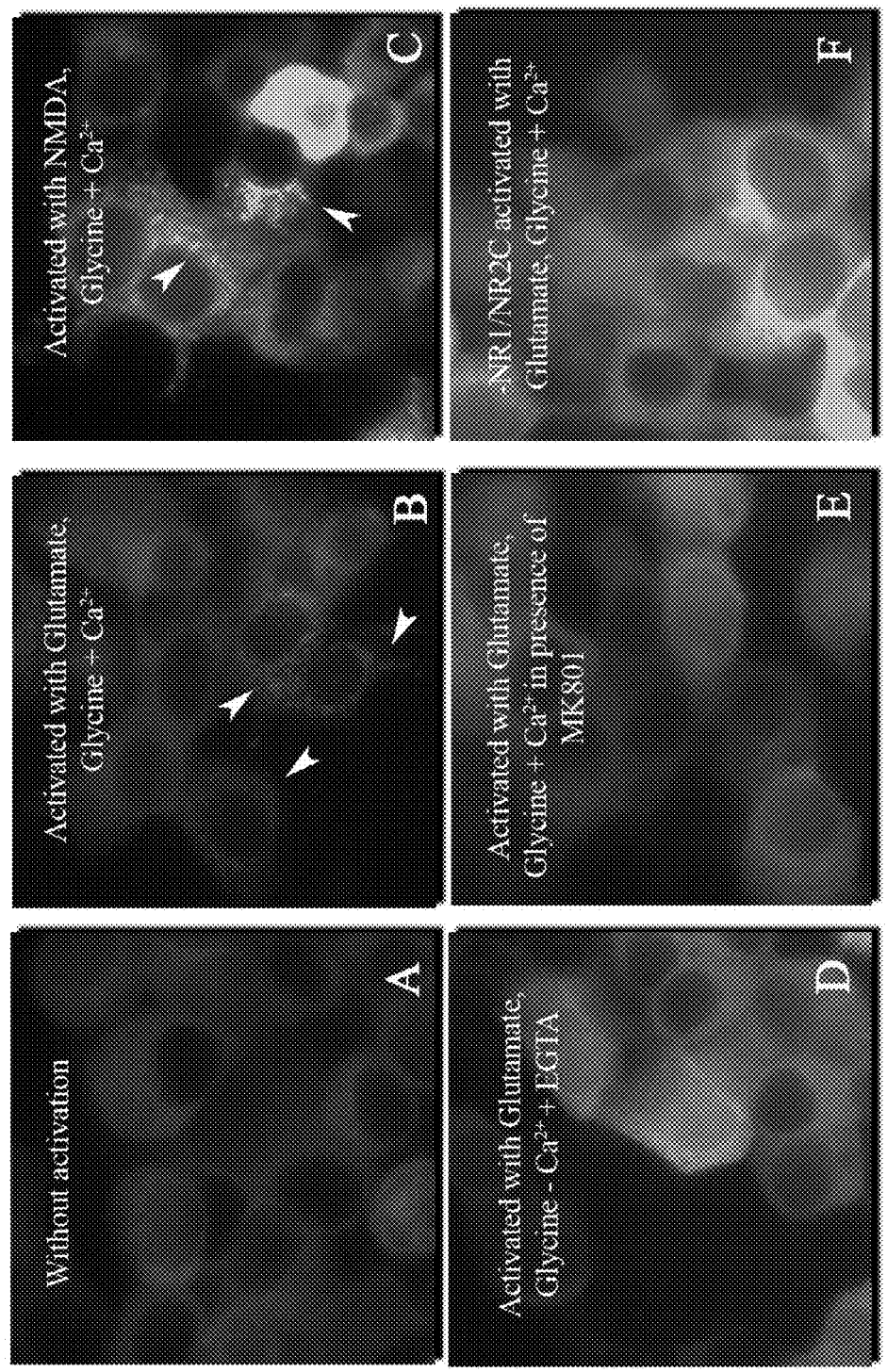
Figure 14:
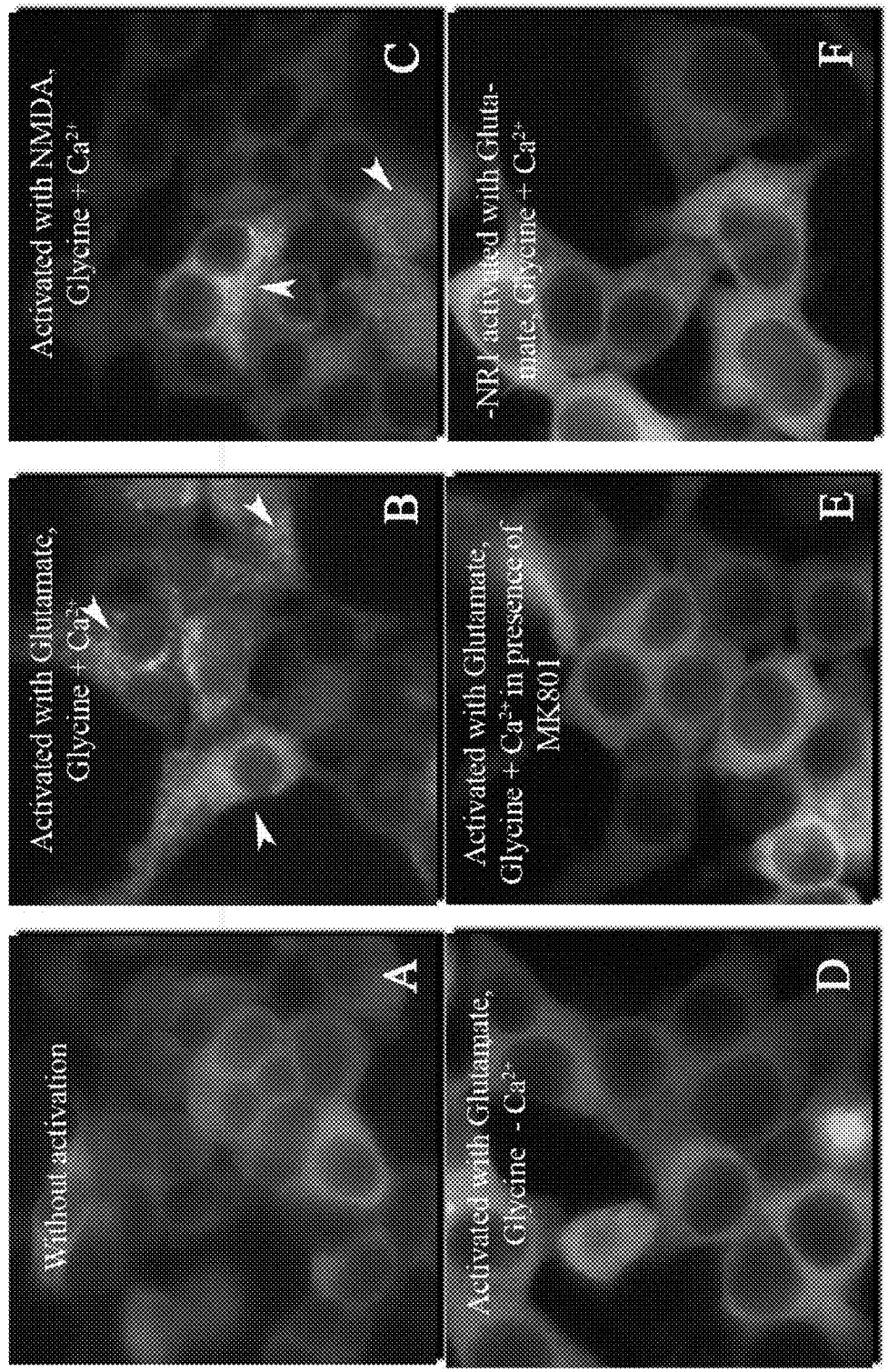
Figure 15:
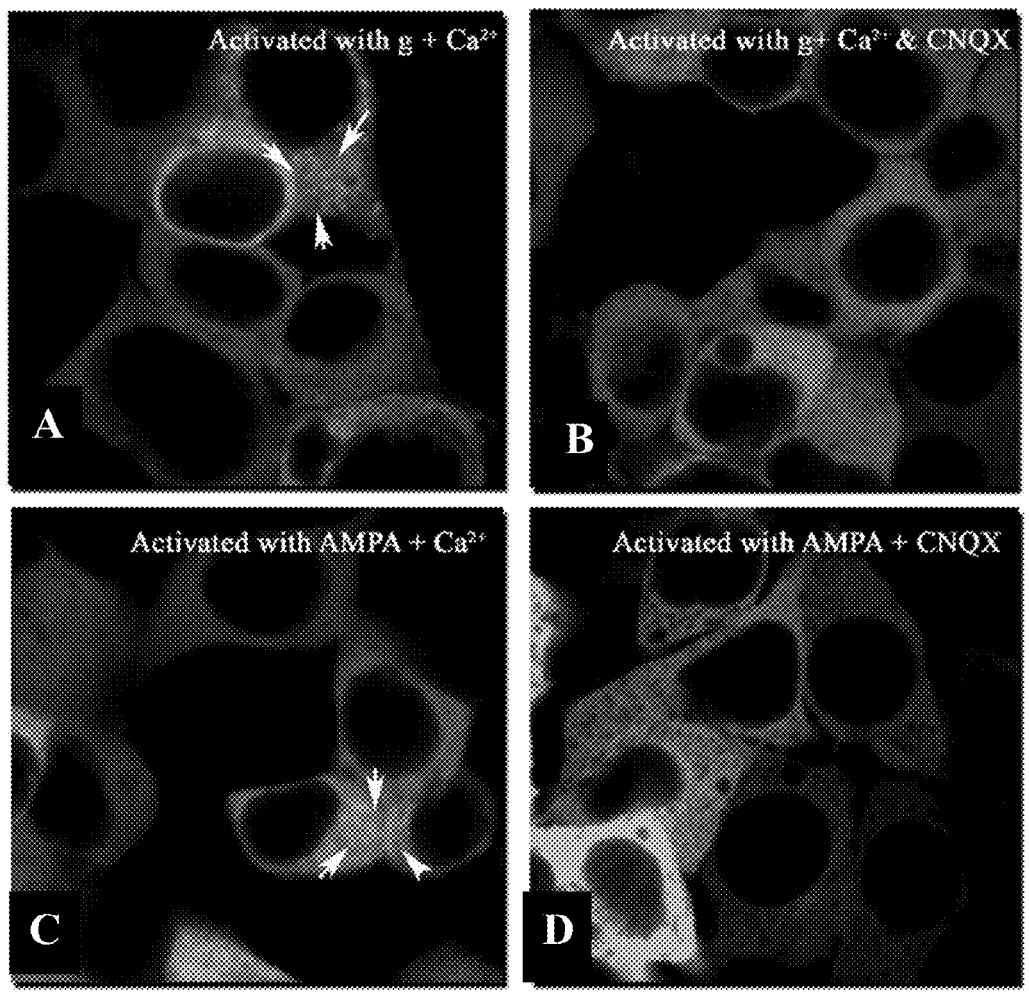
Figure 16:
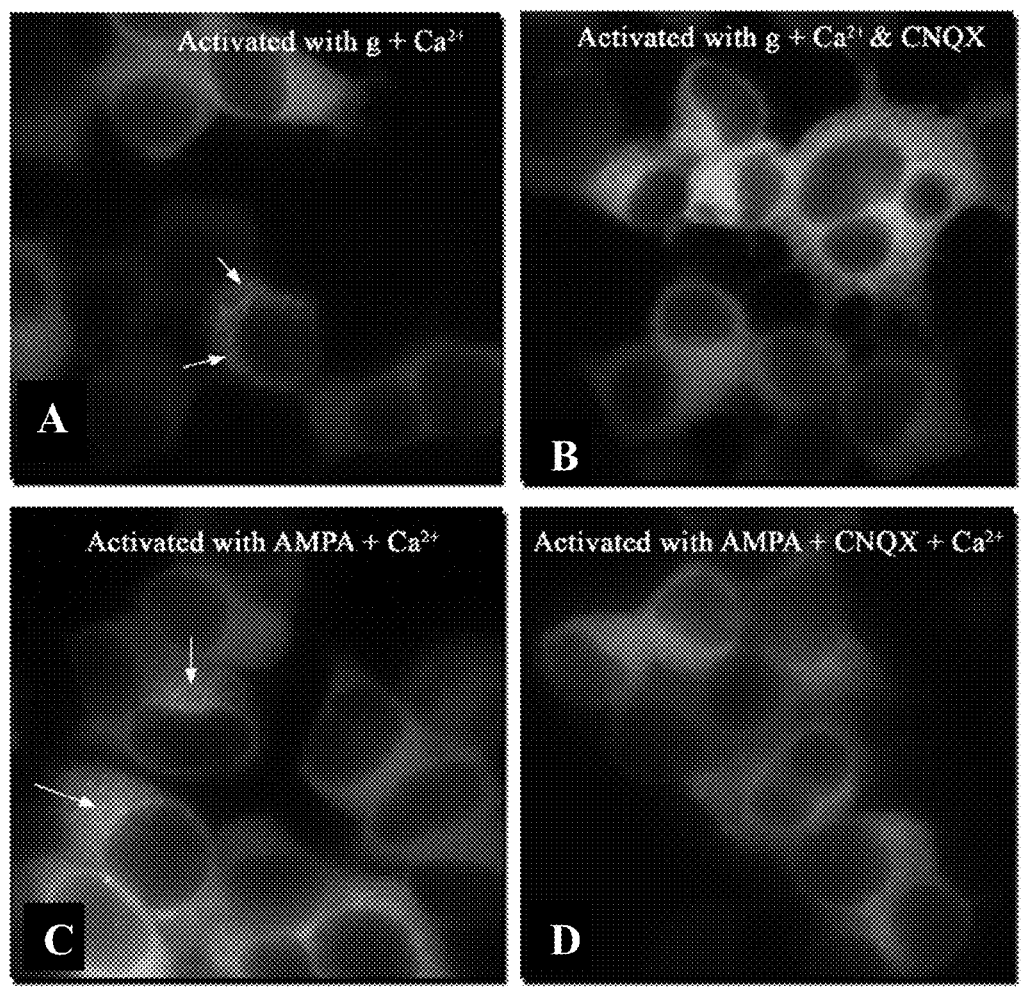
Figure 17:
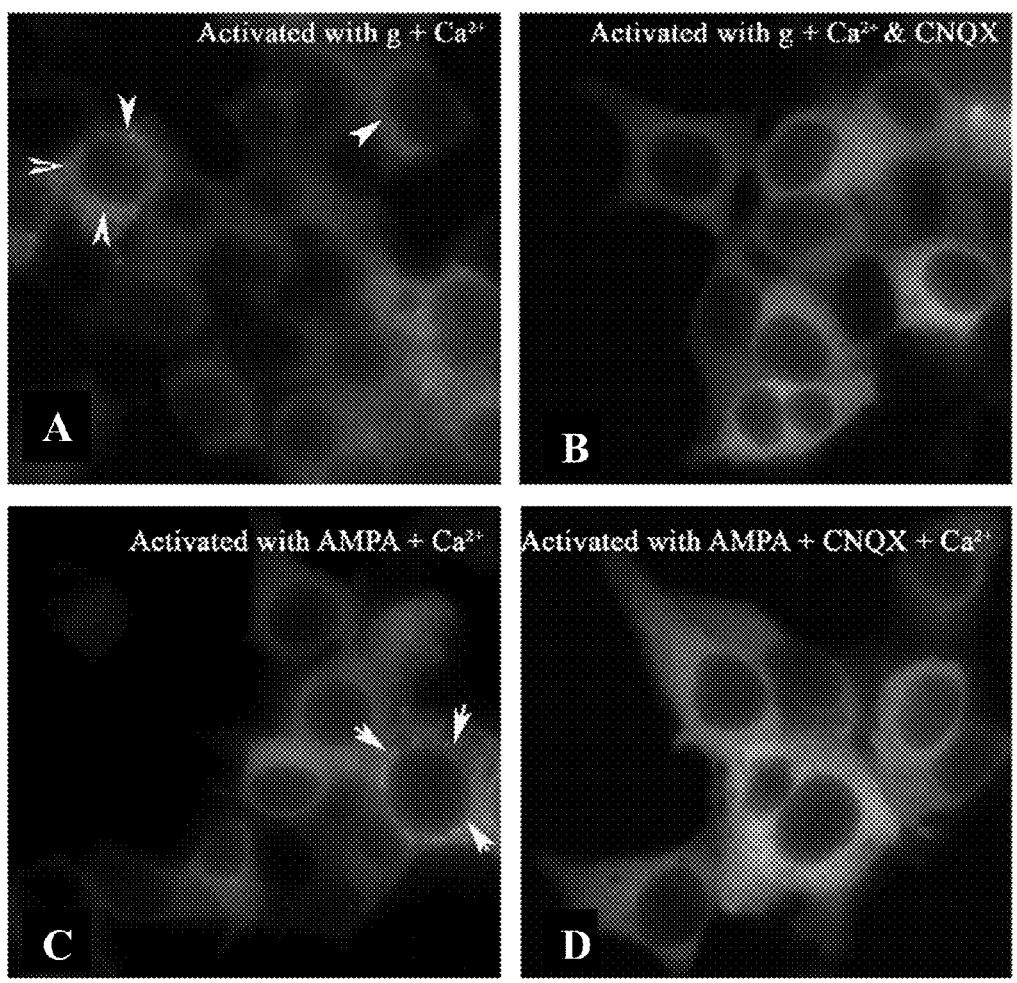
Figure 18:
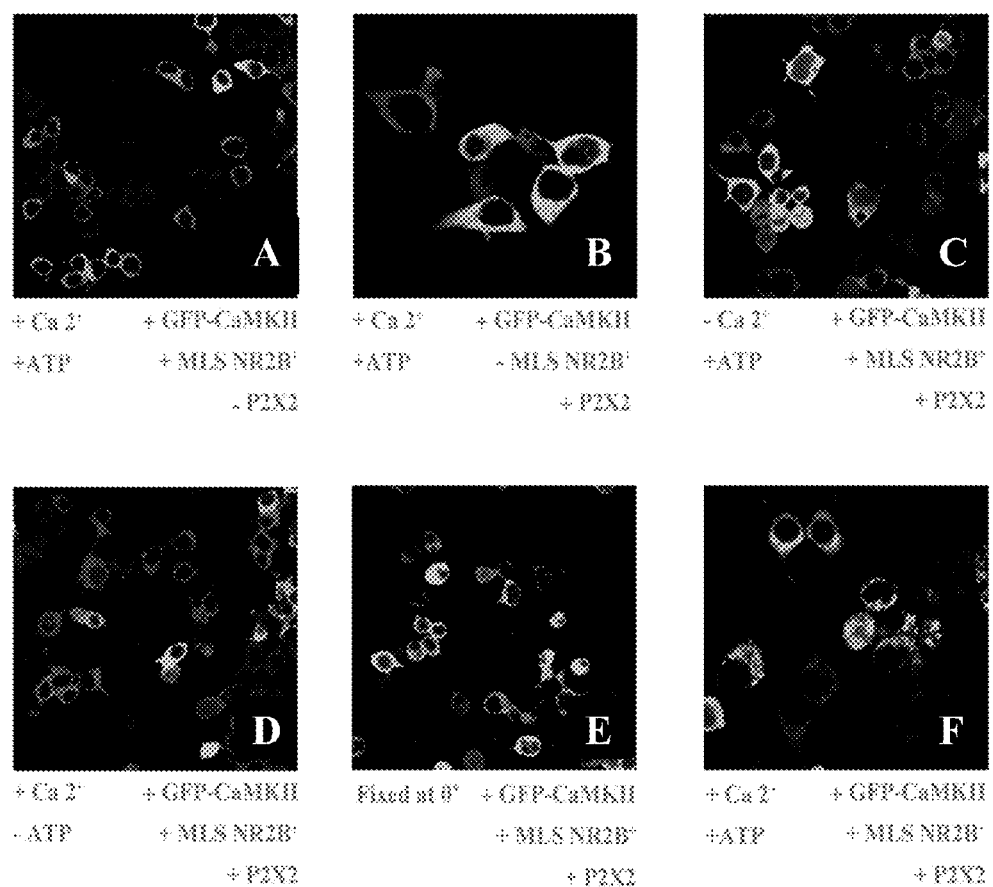
Figure 20:
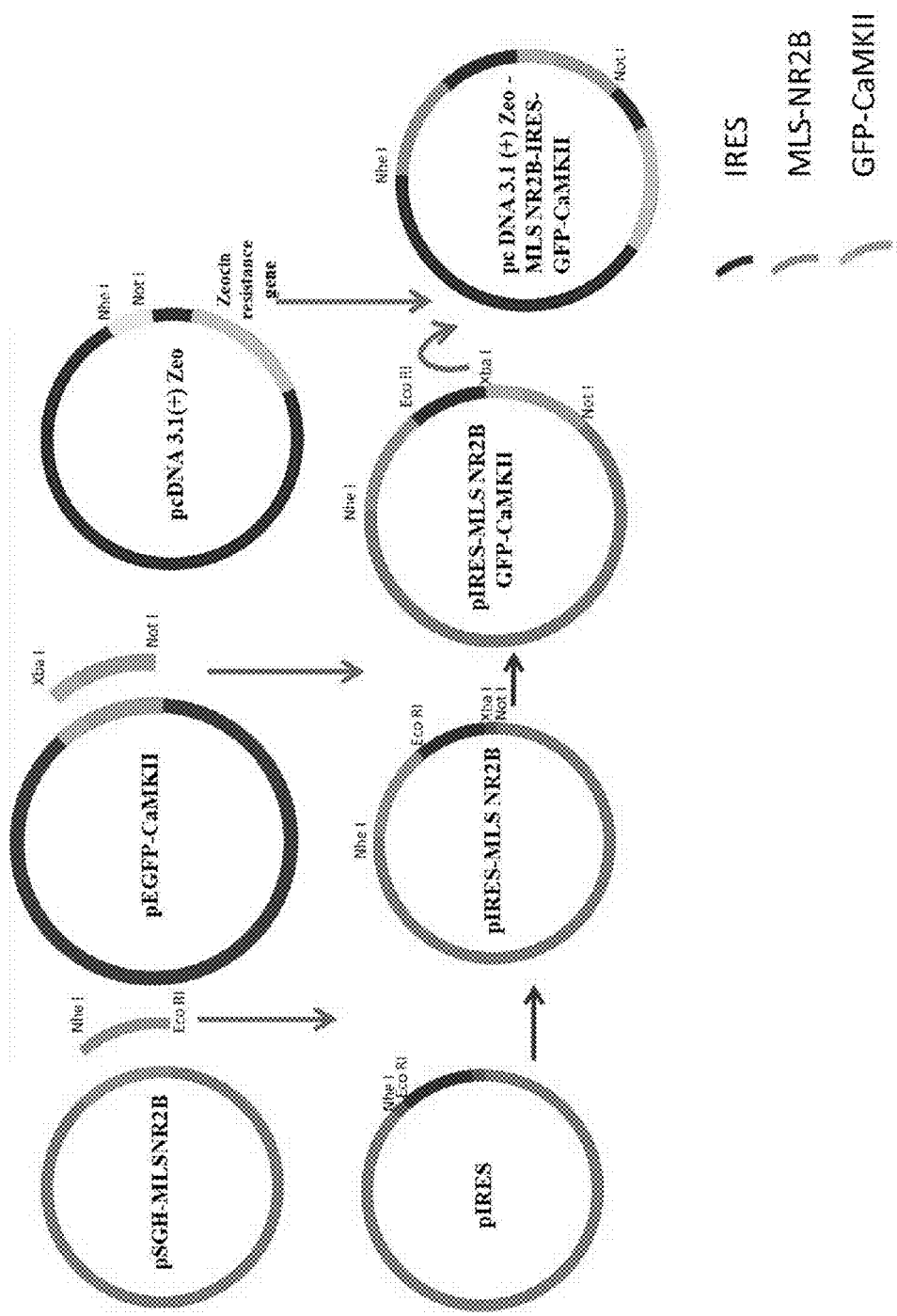
Figure 21A:
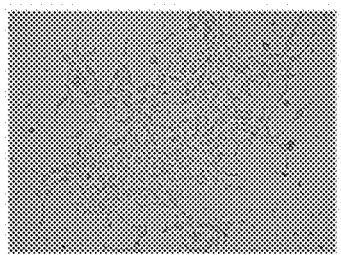
Figure 21B:
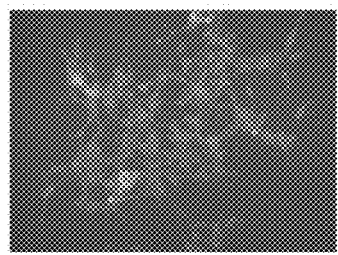
Figure 21C:
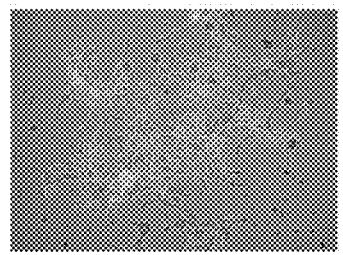
Figure 22:
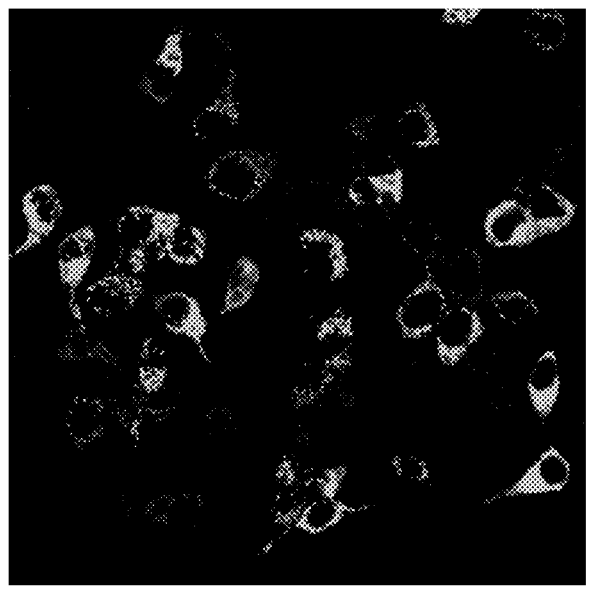

FIG. 12: shows (A) Cavα1c+GFP CaMKII transfected cells activated with ionomycin and calcium and (B) Cavα1c+GFP CaMKII transfected cells without ionomycin in the presence of calcium;

FIG. 13 shows HEK-293 cells co-transfected with NR1 and NR2C subunits of NMDA receptor along with GFP-α-CaMKII and MLS-NR2B, unless indicated otherwise, (A) without activation, (B) activated with glutamate in the presence of glycine and calcium, (C) activated with NMDA in the presence of glycine and calcium, (D) activated with glutamate in the presence of glycine and EGTA, (E) activated with glutamate in the presence of glycine, calcium, and MK801, and (F) cells without NR1 and NR2C subunits transfected therein activated with glutamate in the presence of glycine and calcium;

FIG. 14 shows HEK-293 cells co-transfected with NR1 and NR2D subunits of NMDA receptor along with GFP-α-CaMKII and MLS-NR2B, unless indicated otherwise, (A) without activation, (B) activated with glutamate in the presence of glycine and calcium, (C) activated with NMDA in the presence of glycine and calcium, (D) activated with glutamate in the presence of calcium, (E) activated with glutamate in the presence of glycine, calcium, and MK801, and (F) cells without NR1 subunit transfected therein activated with glutamate in the presence of glycine and calcium;

FIG. 15 shows HEK-293 cells co-transfected with GluR1, GFP-α-CaMKII and MLS-NR2B activated by (A) glutamate or (C) AMPA in the presence of calcium and activated by (B) glutamate or (D) AMPA in the presence of calcium and CNQX;

FIG. 16 shows HEK-293 cells co-transfected with GluR2, GFP-α-CaMKII and MLS-NR2B activated by (A) glutamate or (C) AMPA in the presence of calcium and activated by (B) glutamate or (D) AMPA in the presence of calcium and CNQX;

FIG. 17 shows HEK-293 cells co-transfected with GluR3, GFP-T286D-α-CaMKII and MLS-NR2B activated by (A) glutamate or (C) AMPA in the presence of calcium and activated by (B) glutamate or (D) AMPA in the presence of calcium and CNQX;

FIG. 18 shows HEK-293 cells transfected with GFP-α-CaMKII (A-F), MLS-NR2B (A, C-F) and the cDNA for P2X2 channel (B-F) activated in the presence of (A, B, F) calcium and ATP, (C) ATP alone or, (D) calcium alone. FIG. 18(E) shows cells fixed at time=0;

FIG. 19 shows (A) activation of HEK-293 cells transfected with VGCC subunits (Cavaα1c and β subunits) together with GFP-α-CaMKII and MLS-NR2B by BayK8644 and, (B) HEK-293 cells transfected with VGCC subunits (Cavaα1c and β subunits) together with GFP-α-CaMKII and MLS-NR2B without activation by BayK8644;

FIG. 20 shows construction of the pcDNA 3.1 Zeo vector with MLS-NR2B and GFP-α-CaMKII;

FIG. 21 shows HEK-293 cells transfected with the vector shown in FIG. 20 under zeocin selection shown through (A) bright field microscopy, (B) detection GFP fluorescence, and (C) an overlay of bright field microscopy and GFP fluorescence; and FIG. 22 shows specificity of the calcium signal seen when cells transfected with both MLS-NR2B and GFP-α-CaMKII through the vector shown in FIG. 20 are activated with ionomycin and calcium.

DETAILED DESCRIPTION OF THE INVENTION

The present invention relates to an assay for detecting intracellular binding between two proteins. The assay is useful for detecting intracellular release of free $Ca^{2+}$. In this assay method the transient $Ca^{2+}$ signal is captured by an irreversible protein-protein interaction so that the signal is converted into a form that can be preserved for days to even months. There is absolutely no requirement of any real time signal acquisition or live cell signal acquisition.

Increase in concentration of intracellular free $Ca^{2+}$ ions is a widely used signaling mechanism under various physiological conditions. Release of free $Ca^{2+}$ ions inside the cell happens either through plasma membrane channel proteins that allow $Ca^{2+}$ influx or by release from intracellular $Ca^{2+}$ stores. Since $Ca^{2+}$ release thus becomes the activity of a wide variety of proteins, methods for detection and measurement of intracellular free $Ca^{2+}$ are used as assays for many proteins that are potential drug targets. These methods should be capable of sensing the transient rise in intracellular $[Ca^{2+}]$ and also of generating a detectable signal.

Most of the commonly used methods for $Ca^{2+}$ sensing use molecules that exhibit changes in their fluorescence characteristics upon exposure to increase in $[Ca^{2+}]$. These include small molecular weight macromolecules such as fura-2, indo-1, fluo-3, and Calcium-Green (U.S. Pat. Nos. 4,603, 209 and 5,049,673) as well as proteins such as GFP (green fluorescent protein) family of proteins with a sensor peptide inserted within them (U.S. Pat. No. 6,469,154) or the cameleon molecules of tandem GFP constructs with an intervening $Ca^{2+}$ sensing peptide sequence, that generate a FRET signal upon sensing free $Ca^{2+}$ (U.S. Pat. No. 5,998, 204). In all these existing methods, the fluorescence signal is also as short-lived as the $Ca^{2+}$-transient, and hence signal acquisition in real-time is mandatory. This requires sophisticated equipments with increased temporal resolution and capability for real time measurements from live cells. Moreover this also imposes rapid liquid dispensing. Consequently the cost of instrumentation becomes significantly high as well as the choice of equipments that can be used becomes limited. In addition severe constraints are imposed for carrying out these assays at high throughput scale. U.S. Pat. No. 6,514,709 disclosed a method that prolongs the duration of the $Ca^{2+}$-transients by incorporating an intracellular chelator that alters the kinetics of signal generation, so that the signal is prolonged. Even then, measurements will have to be done on cells in the live condition.

Figure 1:
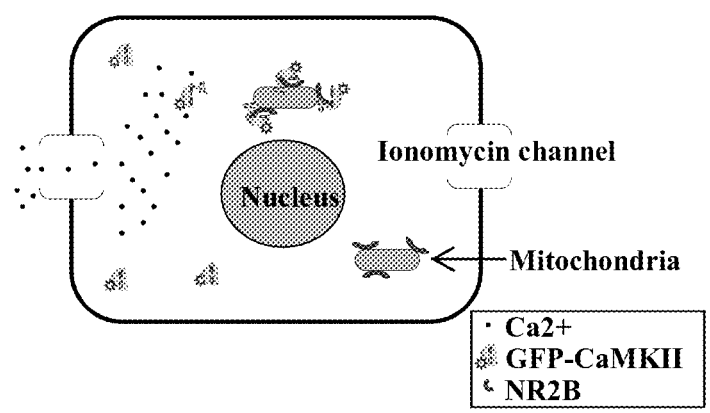
FIG. 1 is a schematic representation of the assay system for detection of release of intracellular free Ca$^{2+}$.

$Ca^{2+}$/calmodulin dependent protein kinase type II (CaMKII) present at neuronal synapses, upon activation by increase in intracellular $Ca^{2+}$, gets translocated to the NMDA-type glutamate receptor and binds irreversibly by its T-site (the $Thr^{286}$-binding site) to the NR2B subunit of the receptor. A GFP-fusion of CaMKII (GFP-CaMKII) and a fusion of the binding sequence on NR2B with a mitochondrial targeting sequence (MLS-NR2B) upon co-transfection in HEK-293 cells, bind to each other in response to increase in intracellular $Ca^{2+}$. GFP-CaMKII present in the cytosol translocates to mitochondria, where it binds to MLS-NR2B. FIG. 1 depicts schematically the appearance of punctae of green fluorescence in cells which had a uniform distribution of green fluorescence before stimulation with $Ca^{2+}$. To demonstrate this phenomenon, intracellular $Ca^{2+}$ influx was generated by adding the ionophore, ionomycin, which binds to the cell membrane and forms pores through which extracellular $Ca^{2+}$ flows in. This is a combination of two published methods (Strack, S., McNeill, R. B., and Colbran, R. J., 2000, J Biol Chem 275, 23798-23806; Bayer, K. U., LeBel, E., McDonald, G. L., O'Leary, H., Schulman, H. and De Koninck, P., 2006, J. Neurosci. Vol. 26, p 1164-1174) but is not identical to either.

Surprisingly it has been found that the percentage of green cells that formed green punctae increases with increase in concentration of extracellular $Ca^{2+}$ provided. At higher concentrations of extracellular $Ca^{2+}$, more cells formed green punctae. Since extracellular concentration of $Ca^{2+}$ is related to the concentration of intracellular $Ca^{2+}$ levels in the system, it is possible to quantitate intracellular free $Ca^{2+}$ concentration.

Since the signal from fluorescent $Ca^{2+}$-sensing dyes is also as short lived as the increased $Ca^{2+}$ levels, the commonly used methods require sophisticated equipments with increased temporal resolution and capability for real time measurements from live cells. This not only necessitates the use of more expensive equipments but also limits the choice of equipments that can be used. For example in case of fluorescence microscope, only inverted microscope could be used. On the contrary, the interaction between CaMKII and NR2B is irreversible and hence produces a stable signal corresponding to a transient increase in intracellular $Ca^{2+}$ thereby eliminating the necessity for real time measurements. After completing the experiment on cover slips in multi well cell culture plates, the cells can be fixed and mounted on slides and can be viewed in an upright or inverted fluorescence microscope. Since the method disclosed in the present invention is not dependent on real time data acquisition techniques it is useful in drug discovery program by adapting it for high throughput screening for compounds that inhibit proteins which cause increase in intracellular $[Ca^{2+}]$ such as $Ca^{2+}$-channel proteins. Moreover, the method disclosed in the present invention could enable many more laboratories with lesser instrumentation, to take up investigations on events and proteins that cause increase in intracellular $[Ca^{2+}]$.

GFP-α-CaMKII was constructed in the vector, pEGFP of Clontech, using the cDNA of CaMKII obtained as a gift from Prof. Mary B. Kennedy of the Division of Biology, California Institute of Technology, Pasadena, USA (Praseeda M., Pradeep K. K., Krupa A., Krishna S. S., Leena S., Kumar R. R., Chemyan J., Mayadevi M., Srinivasan N. and Omkumar R. V., 2004, Biochem J, 378, 391-397).

MLS-NR2B was constructed in the vector pSGH, obtained as gift from Dr. Stefan Strack, Department of Pharmacology, University of Iowa, USA (Strack, S., McNeill, R. B., and Colbran, R. J. (2000) J Biol Chem 275, 23798-23806) using the cDNA of NR2B obtained as a gift from Prof. S. Nakanishi, Graduate School of Medicine and Faculty of Medicine, Kyoto University, Department of Biological Sciences, Kyoto, JAPAN. The cDNA encoding NR2A also was a gift from Prof. S. Nakanishi, Department of Biological Sciences, Kyoto University, JAPAN. The mammalian expression vectors for NR1 (pRc-NR1), NR2A and NR2B (pRK-NR2A and pRK-NR2B) were gifts from Dr. David Lynch, Children's Hospital of Philadelphia, USA. The cDNA of vanilloid receptor type 1 (VR1), also known as TRPV1 (Caterina et al., 1997, Nature, Vol. 389, p 816-824) was a provided by Dr. David Julius, Department of Physiology, University of California San Fransisco, San Fransisco, Calif. 94158-2517, USA. The cDNA of glutamate receptor, was provided by Prof. Peter Seeberg, Department of Molecular Neurobiology, Max Planck Institute for Medical Research, D-69120 Heidelberg, Germany.

Experimental Procedures

Generation of Expression Constructs for the Fusion Proteins Having the Phosphorylation Sites on NR2A or NR2B, Conjugated to Mitochondrial Localizing Signal Sequence The cDNAs of NR2A (encoding amino acid residues 1265-1301) or NR2B (encoding amino acid residues 1271-1311) harboring the phosphorylation site for CaMKII ($Ser^{1291}$ and $Ser^{1303}$ of NR2A and NR2B respectively) present between the BamHI and EcoRI sites in pGEX-2T-NR2A or pGEX-2T-NR2B vectors (Praseeda, M., Mayadevi, M., and Omkumar, R. V., 2004, Biochem. Biophys. Res. Commun. 313, 845-849) were subcloned into the pSGH vector. The sequences of NR2A and NR2B form parts of fusion proteins with a mitochondrial targeting signal sequence, a myc-epitope and GST at the N-terminal end (MLS-NR2A or MLS-NR2B). The sequences of the fusion constructs were confirmed by DNA sequencing of the NR2A or NR2B segments.

Generation of Mammalian Expression Constructs of α-CaMKII

The cDNA of α-CaMKII was amplified by PCR from pGEM2α (Praseeda M., Pradeep K. K., Krupa A., Krishna S. S., Leena S., Kumar R. R., Chemyan J., Mayadevi M., Srinivasan N. and Omkumar R. V., 2004, Biochem J, 378, 391-397) using forward primer having nucleotide sequence as set forth in SEQ ID NO: 1 and reverse primer having nucleotide sequence as set for the in SEQ ID NO: 2 to yield a PCR product with KpnI and BamHI sites at 5' and 3' ends respectively. The PCR product was cloned into pEGFP-C1 vector (Clontech) using the corresponding restriction sites in the multiple cloning site of the vector, which resulted in an N-terminal GFP-fusion of α-CaMKII (GFP-α-CaMKII).

```
                                           SEQ ID NO: 1
        5'-CGGGGTACCATGGCTACCATCACCTGC-3'

SEQ ID NO: 2
        5'-CGCGGATCCCTATCAATGGGGCAGGACGG-3'
```

Site-Directed Mutagenesis

Site-directed mutagenesis was carried out using the QuikChange Site-Directed Mutagenesis Kit from Stratagene based on Kunkel's method (Kunkel, T. A., 1985, Proc. Natl. Acad. Sci. USA 82, 488-492). The cDNA of α-CaMKII present in the expression vector pEGFP-C1-α-CaMKII served as the template to generate mutants. The NR2A or NR2B sequences present in the pSGH-NR2A or pSGH-NR2B expression vectors were also used as templates to generate mutants.

Transfection, $Ca^{2+}$-Stimulation and Imaging

HEK-293 (Human Embryonic Kidney) cells were cultured as monolayer in DMEM containing 10% FBS and antibiotics (penicillin 100 units/ml, streptomycin 100 μg/ml, fungizone 2.5 μg/ml) at 37° C. in a humid atmosphere having 5% $CO_2$.

For transfection, $1.5 \times 10^4$ HEK-293 cells were seeded on sterile 12 mm cover slips in 24 well plates (Nunc). After 24 hrs, the cells were cotransfected with plasmid constructs encoding GFP-α-CaMKII (0.1 μg/well) and either of MLS-NR2A or MLS-NR2B (0.25 μg/well), or pRK-NR2A or pRK-NR2B (along with pRc-NR1 for expression of functional NMDA receptor) using Lipofectamine reagent. About 48 hrs following transfection, cells were washed with Hank's balanced salt solution (HBSS) containing 20 mM HEPES and 1.4 mM EGTA. The cells were then incubated with 15 μM ionomycin in the same buffer for 10 min. Subsequently the cells were incubated in the same buffer containing 2 mM $CaCl_2$ and 3 μM ionomycin. Cells were fixed with 3.7% paraformaldehyde in PBS (Phosphate-buffered saline, 10 mM disodium hydrogen phosphate, 1.8 mM potassium dihydrogen orthophosphate, 140 mM sodium chloride, 2.7 mM potassium chloride, pH adjusted to 7.4) at different time points after addition of calcium, mounted with mountant containing DABCO (antifade) and were observed through either a simple fluorescence microscope or a confocal fluorescence microscope (TCS-SP2-AOBS from Leica).

Appearance of perinuclear granules due to mitochondrial localization of GFP-α-CaMKII is taken as the signal for binding between GFP-α-CaMKII and MLS-NR2B. In case of binding between GFP-α-CaMKII and full-length NR2B, accumulation of GFP-fluorescence in the membraneous structures such as nuclear membrane, endoplasmic reticulum membrane, plasma membrane, etc is taken as signal for binding. Data presented are for cells fixed immediately after incubation with 15 µM ionomycin (−Ca$^{2+}$ influx) or 2-5 minutes after Ca$^{2+}$ stimulus (+Ca$^{2+}$ influx). The total number of green fluorescent cells and cells which develop the signal for binding were counted manually for each microscopic field. Number of cells that develop signal for binding is represented as percentage of total number of green fluorescent cells (number of green fluorescent cells which develop signal for binding + number of green fluorescent cells which do not develop signal) in a field. Average for at least three separate fields was obtained for each experiment. Mean±standard deviation of data obtained from three such experiments is presented as values in inset in FIG. 2. Wherever images for lack of binding are presented, no cell was found to develop the perinuclear granules in repeated experiments and hence no quantitation data is presented.

NMDA Receptor Activity Assay

For expression of NMDA receptor (NMDAR), the cells were cotransfected with plasmid constructs encoding GFP-α-CaMKII (0.1 µg/well) and NR1 (pRc-NR1 plasmid) and NR2B (pRK-NR2B plasmid) subunits of NMDAR (0.33 µg/well of pRc-NR1 and pRK-NR2B) using Lipofectamine (Invitrogen). When growth medium was added to the cells, it was supplemented with an inhibitor of NMDA receptor, either 1 mM of 2-amino-5-phosphovaleric acid (AP-5) or 10 µM MK-801. For detecting activity of NMDAR, about 48 hrs following transfection, cells were washed twice with Ca$^{2+}$ and Mg$^{2+}$ free Hank's balanced salt solution (HBSS). The cells were then incubated with HBSS solution containing glutamate (10 µM) and glycine (2 µM), with or without CaCl$_2$ (2 mM) for about 5 minutes. Cells were fixed with 3.7% paraformaldehyde in PBS for about 10 to 15 minutes and were washed thrice with PBS. The fixed cells were mounted onto glass slides.

In experiments with NMDAR containing NR2A subunit, cells were co-transfected with plasmid constructs encoding GFP-α-CaMKII (0.1 µg/well) and NR1 (pRc-NR1 plasmid) and NR2A (pRK-NR2A plasmid) subunits of NMDAR (0.33 µg/well of pRc-NR1 and pRK-NR2A) along with MLS-NR2B (0.33 µg/well of pSGH-NR2B) and growth medium was not supplemented with AP-5. NMDAR activity was detected as described in the previous section.

TRPV1 Receptor Activity Assay

For the expression of TRPV1, HEK-293 cells were cotransfected with TRPV1 (pCDNA3-TRPV1, about 0.2 µg/well), MLS-NR2B (pSGH-MLS-NR2B, about 0.33 µg/well) and GFP-CaMKII (pEGFP-CaMKII, about 0.1 µg/well) using lipofectamine reagent. After 48 hours, the transfected cells were subjected to TRPV1 activity assay. The growth medium was removed and the cells were washed with Ca$^{2+}$ and Mg free HBSS containing 400 µM EGTA. The receptor was activated with 3 µM or 10 nM of capsaicin with 2 mM Ca$^{2+}$ in HBSS without Mg$^{2+}$ for 5 minutes. Control without Ca$^{2+}$ during activation was also performed. The inhibitor of TRPV1 receptor, capsazepine (50 µM), when used, was preincubated for 3 minutes with cells in Ca$^{2+}$ and Mg$^{2+}$-free HBSS followed by activation using the components as described above with 50 µM capsazepine. Cells were then fixed and were mounted onto glass slides.

GluR4 Receptor Activity Assay

HEK-293 cells were cotransfected with GluR4 (pRK5-GluR4, about 0.33 µg/well), MLS-NR2B (pSGH-MLS-NR2B, about 0.33 µg/well) and GFP-CaMKII (pEGFP-CaMKII, about 0.1 µg/well) using lipofectamine reagent. During growth, the medium was supplemented with 50 µM CNQX (inhibitor of AMPA receptor). After 48 hours, the transfected cells were subjected to GluR4 activity assay. The growth medium was removed and the cells were washed twice with Ca$^{2+}$ and Mg free HBSS containing 2 mM HEPES and 400 µM EGTA. The GluR4 receptor was activated with HBSS solution containing 10 µM glutamate with or without 2 mM Ca$^{2+}$ for about 5 minutes. The inhibitor, CNQX (50 µM), when used, was preincubated for 3 minutes with cells in Ca$^{2+}$ and Mg$^{2+}$-free HBSS followed by activation using the components as described above with 50 µM CNQX. Cells were then fixed and were mounted onto glass slides.

Basic System for Detection of Intracellular Ca$^{2+}$-Release

Figure 2:
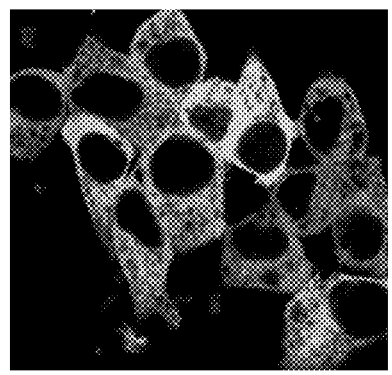
FIG. 2 shows Ca$^{2+}$-dependent generation of signal due to GFP-α-CaMKII translocation towards mitochondrially localized NR2B sequence (MLS-NR2B) observed as the appearance of punctae.
Figure 2:
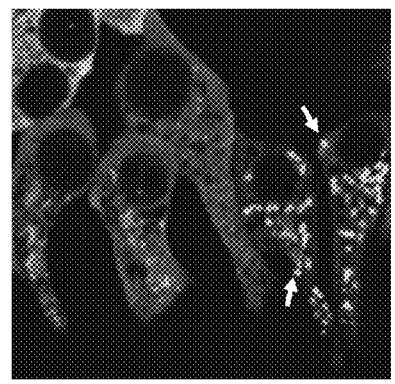
Figure 2:
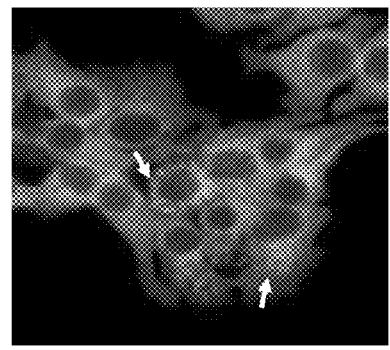
Figure 4:
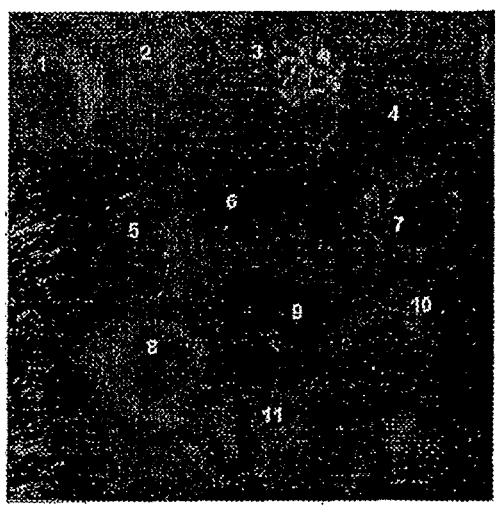
FIG. 4 shows two images of cells, one obtained after inducing Ca$^{2+}$-influx to cells (Image 1) and the other obtained without inducing any Ca$^{2+}$-influx (Image 2)
Figure 4:
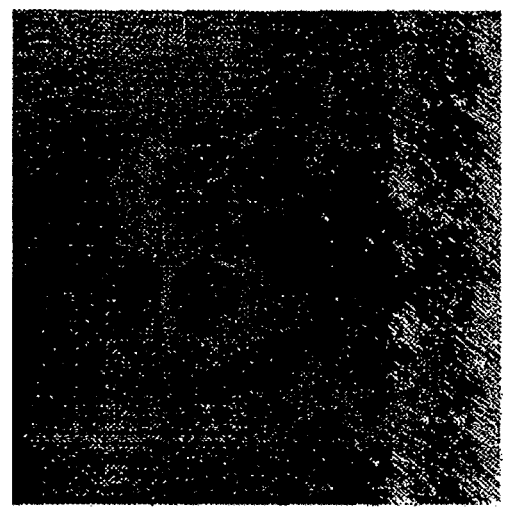

The system described in FIG. 1 was imaged by confocal and non-confocal fluorescence microscopes and the images are presented in FIG. 2. The arrows in the Plus-Ca$^{2+}$ images indicate the cells which develop punctate appearance due to mitochondrial localization of GFP-α-CaMKII, consequent to intracellular rise in [Ca$^{2+}$]. Quantification of cell count carried out as described in FIG. 4 is shown in the confocal Plus-Ca$^{2+}$ image.

Figure 3:
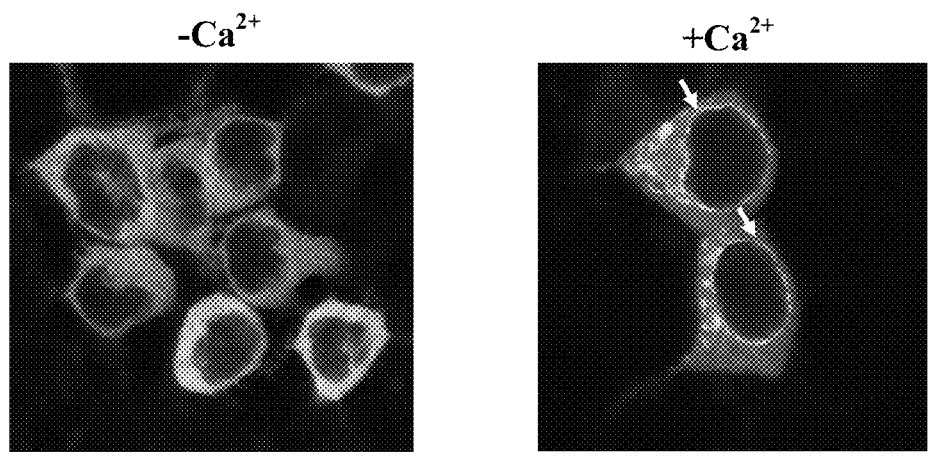
FIG. 3 shows Ca$^{2+}$-dependent generation of signal due to GFP-α-CaMKII translocation towards full-length NR2B localized on intracellular membranous organelles.

Development of Ca$^{2+}$-Dependent Signals by Using Full-Length NR2B Instead of MLS-NR2B The data in FIG. 3 is obtained by transfecting cells with full-length NR2B instead of MLS-NR2B. Since full length NR2B is localized to nuclear and other intracellular membranes, GFP-CaMKII localizes to those membraneous structures instead of mitochondria, upon sensing increase in intracellular [Ca$^{2+}$].

Quantitation of the Intracellular Ca$^{2+}$-Dependent Signal

Figure 5:
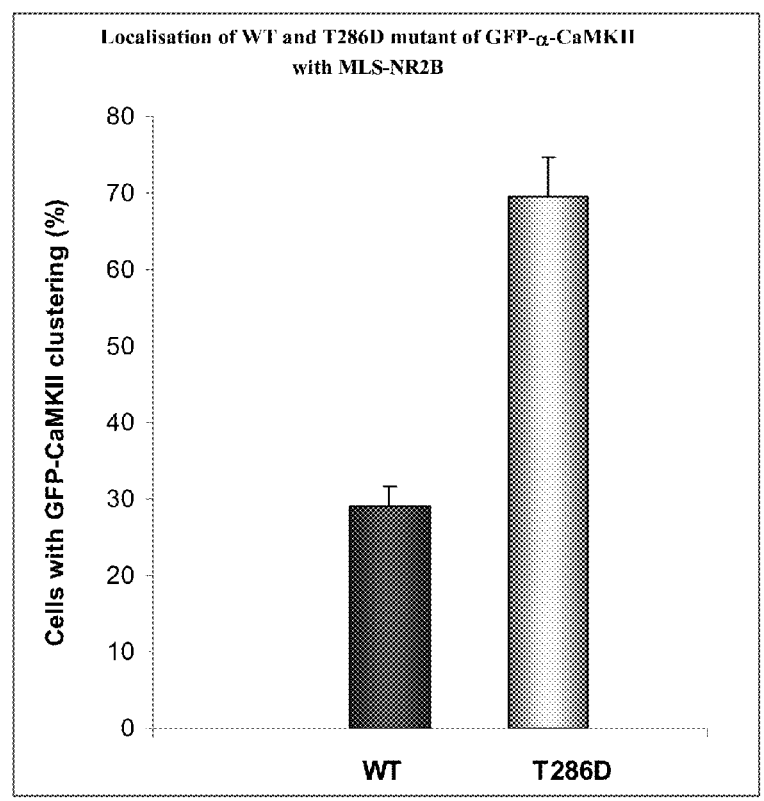
FIG. 5 shows the quantitation data obtained as described in FIG. 4, for the wild-type and T286D mutant forms of GFP-α-CaMKII.
Figure 6:
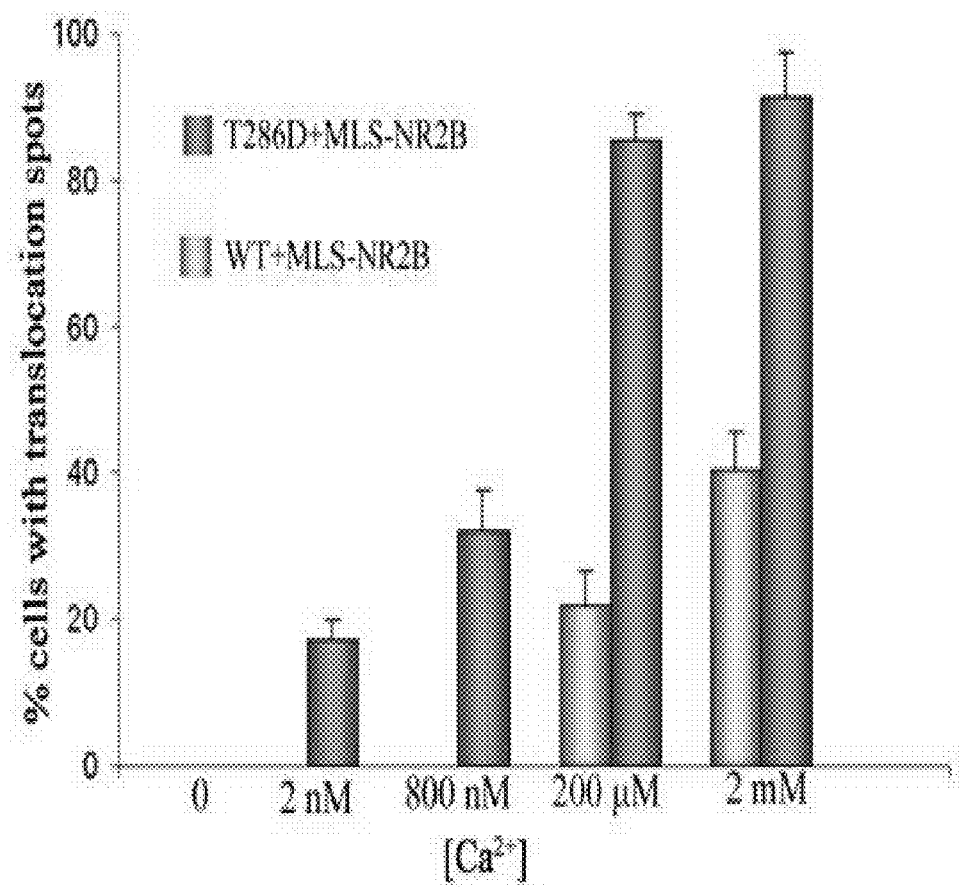
FIG. 6 shows the quantitation data obtained as described in FIG. 4, for the wild type and T286D mutant forms of GFP-α-CaMKII, at different concentrations of Ca$^{2+}$ in the extracellular medium.

The inventors have found that the number of cells that develop the GFP-clustering signal is dependent on the concentration of extracellular Ca$^{2+}$ and hence the intracellular Ca$^{2+}$ (FIG. 6). It also depends on the efficiency of the binding between CaMKII and NR2B (FIG. 5). The inventors developed a method to express quantitatively the strength of the signal as mentioned in Methods section (Methodology for Transfection, Ca$^{2+}$-stimulation and imaging). Data in FIG. 4 is used to demonstrate this method.

In image 1 of FIG. 4, there are totally 11 cells expressing GFP of which two cells (numbered 3 and 7) show clustering/aggregation of GFP as seen by regions of intense fluorescence. Percentage of cells showing clustering is obtained as 2*100/11=27%.

In image 2, no cells are found to have the GFP clustering, out of the 6 cells expressing GFP.

WT-CaMKII Vs T286D-CaMKII—Cell Count Comparison

The cell count determined as mentioned in methods section as well as in the previous section, for the wild-type and T286D mutant forms of GFP-α-CaMKII are presented in FIG. 5. The T286D mutation which is known to enhance the Ca$^{2+}$/calmoduin affinity of α-CaMKII also improved its efficiency of binding in the intracellular binding system as seen by the increased (more than two fold) cell count (FIG. 5).

[Ca$^{2+}$]-Dependence of Cell Count—WT and T286D-α-CaMKII

Different concentrations of extracellular Ca$^{2+}$ are expected to produce proportional increases in intracellular [Ca$^{2+}$] when ionomycin-mediated Ca$^{2+}$-influx was generated. This was reflected in the cell count obtained for different extracellular [Ca$^{2+}$] (FIG. 6). As [Ca$^{2+}$] increased, the cell count also increased. Moreover the T286D mutant of GFP-α-CaMKII which showed enhanced signal compared to GFP-(WT)-α-CaMKII (FIG. 5) also showed improved sensitivity to [Ca$^{2+}$] as seen by response at lower [Ca$^{2+}$] up to 2 nM. This observation of dependence of the signal on [Ca$^{2+}$] is the key advancement in our invention making this method suitable for sensing intracellular [Ca$^{2+}$] in a semi-quantitative manner.

Figure 7:
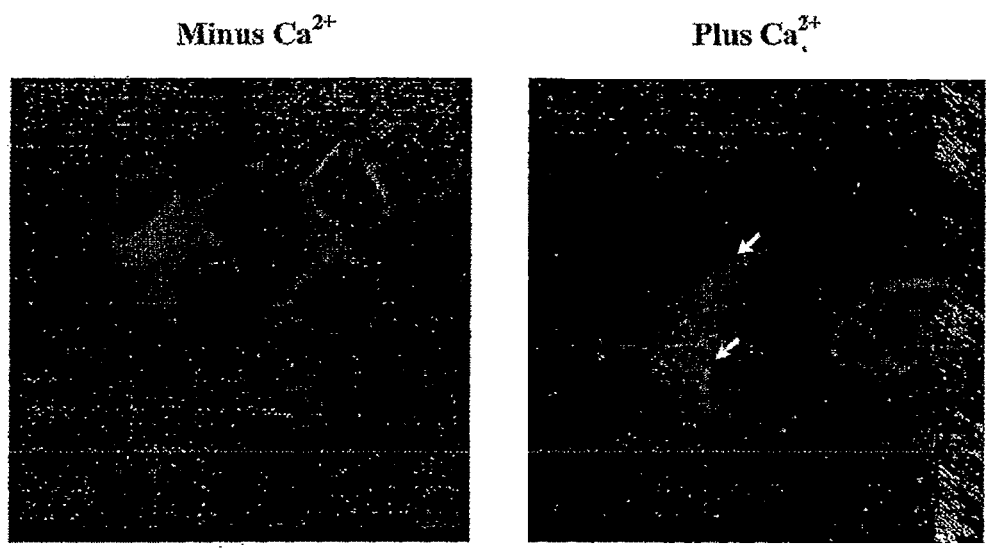
FIG. 7 shows Ca$^{2+}$-dependent generation of signal due to GFP-α-CaMKII translocation towards mitochondrially localized Eag sequence (MLS-Eag)

Mutants of α-CaMKII and NR2B or NR2A that Generate a Localization Signal in Response to Intracellular Release of $Ca^{2+}$ The following pairs of mutants of GFP-α-CaMKII and either of NR2A or NR2B sequences when expressed in HEK-293 cells exhibited. $Ca^{2+}$-dependent binding and generation of localization signals. Some of these pairs generated signals more than the wild-type pair of GFP-α-CaMKII and MLS-NR2B. These could be used either as detection systems with improved sensitivity or under cellular environments where the wild-type pair encounters technical problems such as faulty expression.
1. T286D-α-CaMKII and MLS-WT-NR2B
2. F293E/N294D-α-CaMKII and MLS-WT-NR2B
3. MLS-(S1303A)-NR2B and WT-α-CaMKII
4. S1303A-NR2B and WT-α-CaMKII
5. K42R/T286D-α-CaMKII and MLS-WT-NR2B
6. MLS-Delta$^{IN}$NR2A (deletion of Ile$^{1286}$-Asn$^{1287}$ motif of NR2A) and WT-α-CaMKII
7. MLS-(S1291A)/Delta$^{IN}$ (deletion of Ile$^{1286}$-Asn$^{1287}$ motif of NR2A) NR2A and WT-α-CaMKII
8. MLS-Delta$^{IN}$R2A (deletion of Ile$^{1286}$-Asn$^{1287}$ motif of NR2A) and T286D-α-CaMKII
9. Delta$^{IN}$NR2A (deletion of Ile$^{1286}$-Asn$^{1287}$ motif of NR2A) and T286D-α-CaMKII
10. MLS-K1292A-NR2B and WT-α-CaMKII Interaction of the Binding Site on Eag with GFP-CaMKII for Detection of Intracellular Release of $Ca^{2+}$ The voltage gated potassium channel of *Drosophila* (Eag) that is localised in synapses as well as in axons also interacts at the T-site of CaMKII (Sun, X. X., Hodge, J. J., Zhou, Y., Nguyen, M., and Griffith, L. C. (2004) *J Biol Chem* 279, 10206-10214). The Eag amino acid residues 731-803 (or longer or shorter sequences) which comprise the CaMKII binding motif was cloned into the pSGH vector to obtain an MLS-Eag fusion that could be targeted to mitochondria. When wild-type or suitable mutant forms of GFP-CaMKII coexpressed with wild-type or suitable mutant forms of MLS-Eag were activated with increase in intracellular $Ca^{2+}$, the GFP-CaMKII should translocate to mitochondria giving rise to stable green fluorescent punctae as observed in case of MLS-NR2B. FIG. 7 shows the $Ca^{2+}$-dependent localization of GFP-(WT)-CaMKII to MLS-Eag. This system could also be a $Ca^{2+}$-sensor similar to the CaMKII-NR2B system.

Any peptide sequence which binds to the T-site of CaMKII similar to NR2B could be used as a binding partner for CaMKII in a $Ca^{2+}$-sensing system.

NMDA Receptor Activity

The neuronal N-methyl-D-aspartate (NMDA)-type glutamate receptor is a glutamate activated $Ca^{2+}$-channel that has NR1 and NR2B as subunits.

Figure 8:
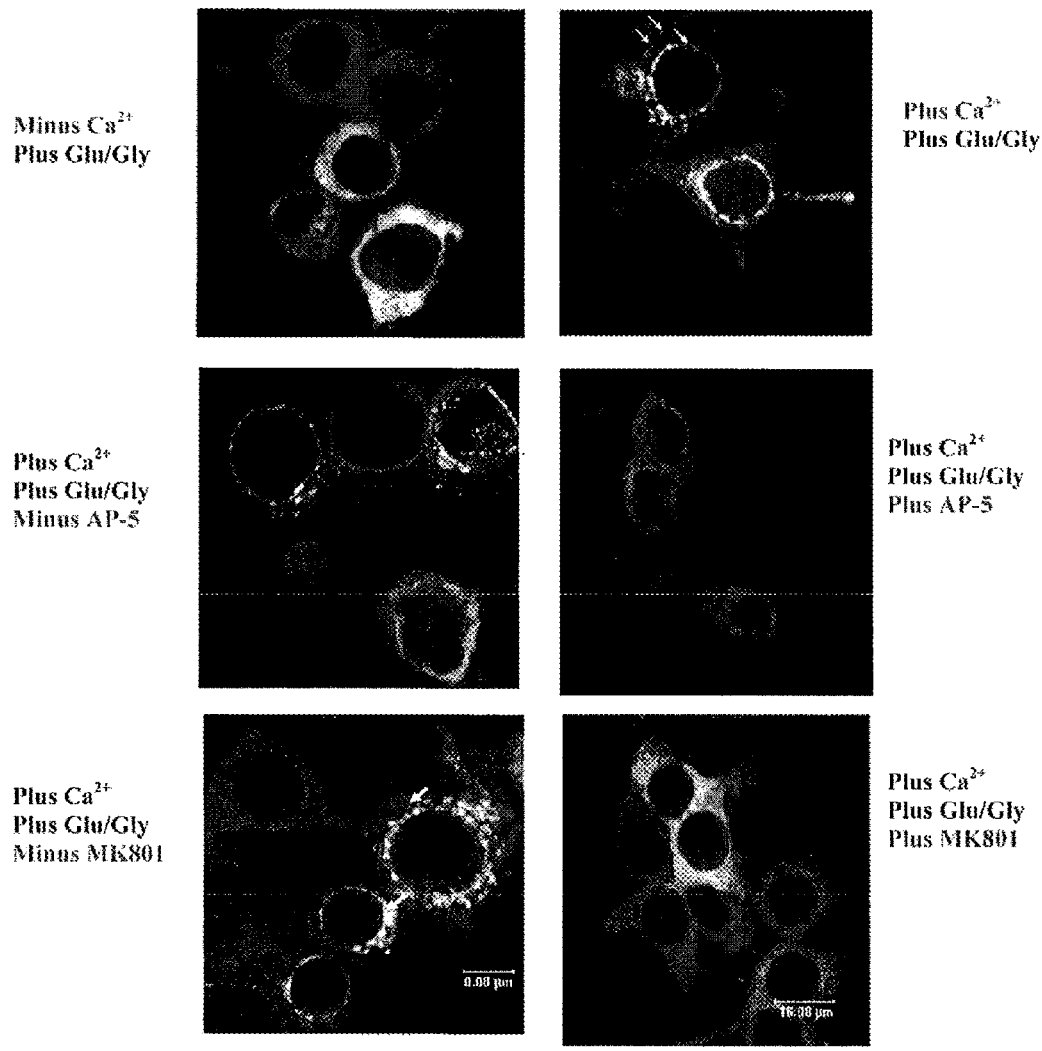
FIG. 8 shows signal generated due to Ca$^{2+}$-influx through NMDA receptor formed of NR1 and NR2B subunits.

When activated with glutamate and glycine it caused influx of $Ca^{2+}$ from the extracellular medium leading to translocation of GFP-α-CaMKII to NR2B that is localized in the nuclear membrane, endoplasmic reticulum and plasma membrane. This signal, shown by arrows in FIG. 8, was not formed in the absence of extracellular $Ca^{2+}$. The signal generation was blocked by the NMDA receptor specific inhibitors, AP-5 and MK-801, further establishing that the signal was specific for the activity of NMDA receptor.

Activity of NMDA Receptor Containing NR2A Subunit

Figure 9:
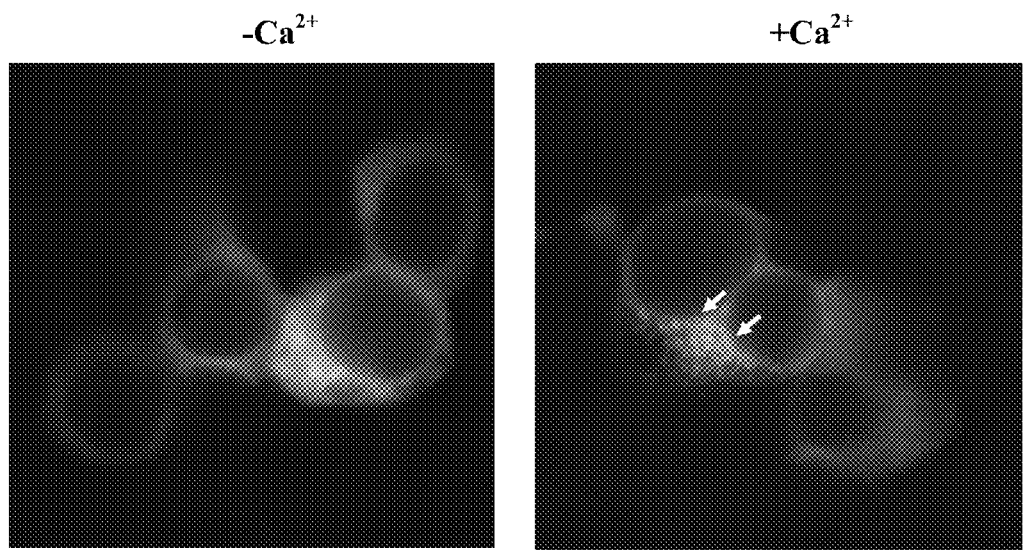
FIG. 9 shows signal generated due to Ca$^{2+}$-influx through NMDA receptor formed of NR1 and NR2A subunits.

Functional NMDAR can be formed by NR1 and NR2A subunit also instead of the NR1/NR2B combination. However, since the NR2A subunit does not bind CaMKII, a translocation signal consequent to influx of $Ca^{2+}$ will not be obtained. By additionally transfecting the mitochondrially localized MLS-NR2B sequence, it is possible to detect the activity of the NR2A-containing NMDAR also in a $Ca^{2+}$-dependent manner. The arrows in FIG. 9 show mitochondrially translocated GFP-α-CaMKII.

Detection and Measurement of the Activity of Other $Ca^{2+}$-Channels

Many other proteins with intracellular $Ca^{2+}$-releasing activity such as $Ca^{2+}$-channel proteins (nicotinic acetylcholine receptor channel (Grando S A, Horton R M, Mauro T M, Kist D A, Lee T X, Dahl M V., J. Invest. Dermatol., 1996, 107, p 412-418), the vanilloid receptor 1 (TRPV1) (Witte D G, Cassar S C, Masters J N, Esbenshade T, and Hancock A A. 2002, J Biomol Screen. 7, p 466-475), G-protein coupled receptors (Fujii, R., Hosoya, M., Fukusumi, S., Kawamata, Y., Habata, Y., Hinuma, S., Onda, H., Nishimura, O., and Fujino, M. 2000, J. Biol. Chem., 275, p 21068-21074), etc. could be expressed in a heterologous cell culture system to generate specific $Ca^{2+}$-channel activity. Activity of all such proteins could also be detected if they are co-expressed with a suitable pair of wild-type or mutant forms of GFP-CaMKII and NR2B, NR2A, Eag or any other protein which binds to the T-site of CaMKII, as described in earlier sections.

Vanilloid Receptor (TRPV1)

Figure 10:
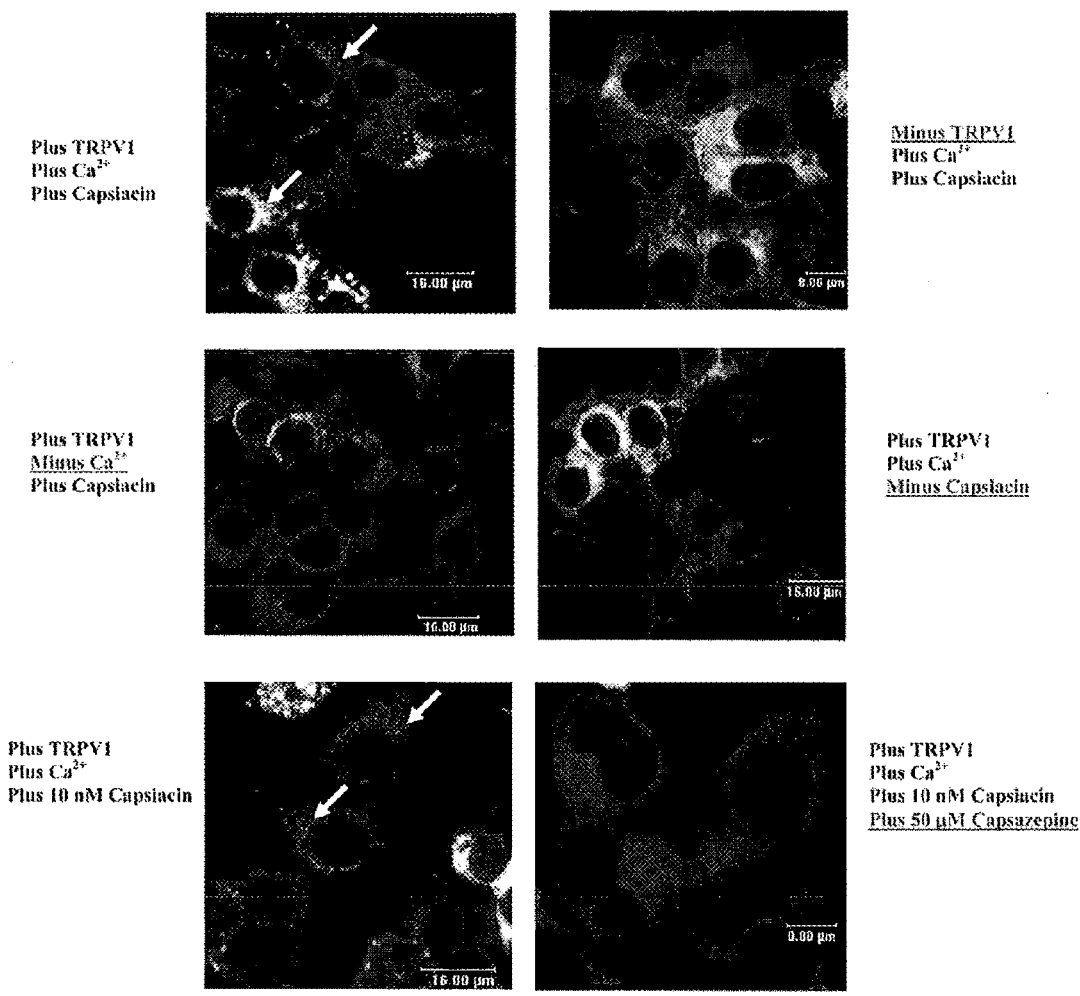
FIG. 10 shows signal generated due to Ca$^{2+}$-influx through vanilloid Receptor (TRPV1)

Vanilloid receptor is a $Ca^{2+}$-channel that is activated by capsaicin, one of the active principle of hot chili peppers (Caterina et al., 1997, Nature, Vol. 389, p 816-824). We have found that the activity of vanilloid receptor (TRPV1) could be detected by our invention for $Ca^{2+}$-sensing. HEK-293 cells cotransfected with TRPV1, GFP-CaMKII and MLS-NR2B upon activation with capsaicin (3 μM or 10 nM), developed green punctae in a $Ca^{2+}$-dependent manner as signal for the $Ca^{2+}$-channel activity of TRPV1 receptor. The signal generation was specific for transfection by TRPV1, activation by capsaicin and also for the presence of $Ca^{2+}$ in the extracellular medium. Signal generation due to activation of TRPV1 could be inhibited by the TRPV1-specific inhibitor capsazepine (FIG. 10). All these results show that the activity of TRPV1 receptor is being detected by our invention.

Neuronal AMPA-Type Glutamate Receptor GluR4

Figure 11:
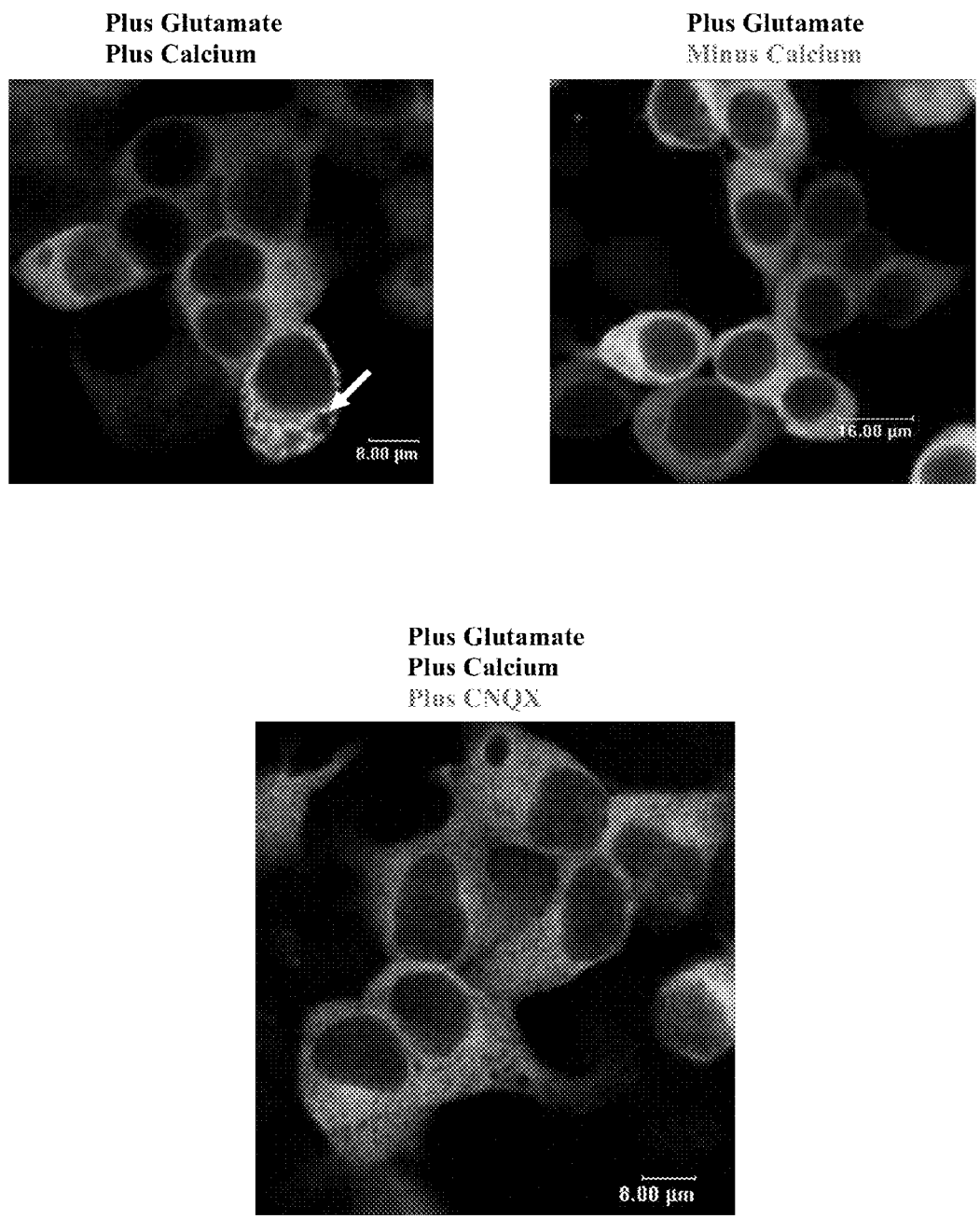
FIG. 11 shows signal generated due to Ca$^{2+}$-influx through the AMPA-type glutamate receptor, GluR4.

The homomeric AMPA-type glutamate receptor formed of the GluR4 subunit causes $Ca^{2+}$-influx upon activation by glutamate (Cushing, et al., 1999, J. Neurosci. Methods. Vol. 90, p 33-36). Upon transfection of HEK-293 cells with the GluR4 subunit along with GFP-CaMKII and MLS-NR2B, it was possible to detect the $Ca^{2+}$-channel activity of the receptor. The receptor was activated by treatment with glutamate which caused the formation of green punctae due to translocation of GFP-CaMKII to mitochondrially localized MLS-NR2B. Generation of the signal could be blocked by the specific inhibitor of the receptor, CNQX (FIG. 11).

System Using an Expression Construct for the Voltage-Gated Calcium Channel Subunit Cavα1c FIG. 12 shows HEK-293 cells transfected with Cavα1c+GFP CaMKII activated with (A) ionomycin and calcium and (B) activated with calcium without ionomycin.

Detection of the Activity of NMDA Receptor Having NR1 and NR2C Subunits

With reference to FIG. 13, HEK-293 cells were co-transfected with NR1 and NR2C subunits of NMDA receptor along with GFP-α-CaMKII and MLS-NR2B (A-E) or without NR1/NR2C (F). About 48 hrs after transfection, the HEK-293 cells were activated with either glutamate (B) or NMDA (C) in the presence of glycine and $Ca^{2+}$. In the same experiment, transfected cells were activated with (D) glutamate in the presence of glycine and EGTA without calcium or (E) glutamate in the presence of glycine, calcium, and MK801. As a control, cells that were not transfected with NR1 and NR2C were activated with glutamate in the presence of glycine and calcium.

Detection of the Activity of NMDA Receptor Having NR1 and NR2D Subunits

With reference to FIG. 14, HEK-293 cells were co-transfected with NR1 and NR2D subunits of NMDA receptor along with GFP-α-CaMKII and MLS-NR2B (A-E) or without NR1 (F). About 48 hrs after transfection, the HEK-293 cells were activated with either glutamate (B) or NMDA (C) in the presence of glycine and $Ca^{2+}$. In the same experiment, transfected cells were activated with (D) glutamate in the presence of glycine and without calcium or (E) glutamate in the presence of glycine, calcium, and MK801. As a control, cells that were not transfected with NR1 were activated with glutamate in the presence of glycine and calcium.

Detection of the Activity of GluR1 Homomer of AMPA Receptor

With reference to FIG. 15, HEK-293 cells were co-transfected with GluR1, GFP-α-CaMKII and MLS-NR2B. About 48 hours after transfection, the cells were activated with (A) glutamate or (C) AMPA in the presence of calcium. Another set of transfected cells was activated by (B) glutamate or (D) AMPA in the presence of calcium and the specific AMPA inhibitor CNQX.

Detection of the Activity of GluR2 Homomer of AMPA Receptor

With reference to FIG. 16, HEK-293 cells were co-transfected with GluR2, GFP-α-CaMKII and MLS-NR2B. About 48 hours after transfection, the cells were activated with (A) glutamate or (C) AMPA in the presence of calcium. Another set of transfected cells was activated by (B) glutamate or (D) AMPA in the presence of calcium and the specific AMPA inhibitor CNQX.

Detection of the Activity of GluR3 Homomer of AMPA Receptor

With reference to FIG. 17, HEK-293 cells were co-transfected with GluR3, GFP-T286D-α-CaMKII and MLS-NR2B. About 48 hours after transfection, the cells were activated with (A) glutamate or (C) AMPA in the presence of calcium. Another set of transfected cells was activated by (B) glutamate or (D) AMPA in the presence of calcium and the specific AMPA inhibitor CNQX.

P2X2 Receptor Assay

With reference to FIG. 18, HEK-293 cells were seeded on coverslips in a 24-well plate and transfected with GFP-α-CaMKII, MLS-NR2B and the cDNA for the purigenic receptor P2X ligand-gated (P2x2) ion channel. The P2X2 channel binds to adenosine triphosphate (ATP) (the ligand for this ligand-gated channel) and is thought to be responsible for mediating synaptic transmission between neurons and between neurons and smooth muscle. The cells transfected with GFP-α-CaMKII, MLS-NR2B, and P2X2 were washed 36 hours afterwards with HBSS containing 1 mM HEPES and 0.5 mM EGTA for five minutes followed by treatment with 100 μM ATP in HBSS (with 1 mM HEPES and 2 mM calcium chloride) for five minutes. Cells not receiving ATP or calcium treatment (FIG. 18C, 18D), or those not transfected with P2X2 or MLS-NR2B (FIG. 18B) were used as negative controls.

FIG. 18 shows ATP-dependent calcium signaling in (A) cells transfected with both GFP-α-CaMKII and MLS-NR2B, but not P2x2, activated by ATP in the presence of calcium; (B) cells transfected with GFP-α-CaMKII and P2x2, but not MLS-NR2B, activated buy ATP in the presence of calcium; (C) cells transfected with GFP-α-CaMKII, MLS-NR2B and P2X2 activated by ATP without calcium; (D) cells transfected with GFP-α-CaMKII, MLS-NR2B and P2X2 in the presence of calcium but not ATP; (E) cells transfected with GFP-α-CaMKII, MLS-NR2B and P2X2 and fixed prior to any activation or exposure to calcium; and (F) cells transfected with GFP-α-CaMKII, MLS-NR2B and P2X2 activated by ATP in the presence of calcium. The results show the localization of the signal as punctae in cells transfected with -α-CaMKII, MLS-NR2B and P2X2 (FIG. 18F). The number of cells with punctae is an indication of calcium influx.

Voltage-Gated Calcium Channel Activity Assay

Figure 19A:
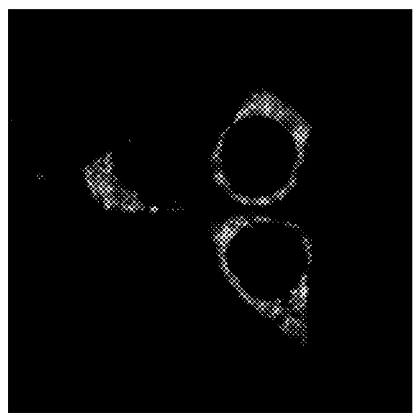
Figure 19B:
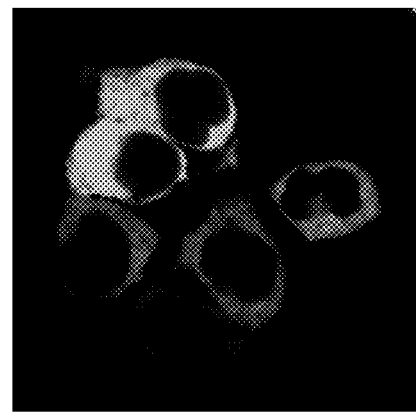

With reference to FIG. 19, HEK-293 cells were transfected with voltage-gated calcium channel (VGCC) subunits (Cavaα1c and β subunits) together with GFP-α-CaMKII and MLS-NR2B. Those cells were then activated by BayK8644, a VGCC agonist, with results shown in FIG. 19A. FIG. 19B shows the same transfected cells, without activation by BayK8644. Cells were fixed for imaging following activation with BayK8644 and in the control condition, and appearance of punctae, based on extracellular $Ca^{2+}$ and transfected VGCC, was assessed. Punctae formation may be inhibited by administration of nifedipine, a specific inhibitor of VGCC.

Formation of Stable Calcium Sensor Clones

With reference to FIG. 20, the pcDNA 3.1 Zeo vector with MLS-NR2B and GFP-α-CaMKII was constructed by cloning the cDNAs for both MLS-NR2B and GFP-α-CaMKII from the parent vectors viz. pSGH-MLS-NR2B and pEGFP-CaMKII respectively into the pIRES vector (Clontech—Cat No: 631605). These cDNAs were inserted into the two multiple cloning sites flanking the internal ribosome entry site (IRES) sequence. pSGH-MLS-NR2B was digested using enzymes Nhe I and Eco RI and MLS-NR2B so released was cloned into the multiple cloning site A of pIRES vector between the same sites. GFP-α-CaMKII was amplified by PCR using pEGFP-CaMKII as the template, forward primer with Xba I restriction site and reverse primer with NotI restriction site, amplified product was digested with the respective enzymes and cloned to the multiple cloning site B of pIRES vector.

SEQ ID NO: 3
(5'-GCTCTAGAATGGTGAGCAAGGGC-3')-
forward primer for GFP

SEQ ID NO: 4
(5'-ATAAGAATGCGGCCGCTCATCAATGGGGCAGGACGGAGG-
3')-
reverse primer for CaMKII The whole reading frame incorporating the single mRNA coding for MLS-NR2B-IRES-GFP-α-CaMKII was then excised from the pIRES-MLS-NR2B-GFP-α-CaMKII using restriction enzymes Nhe I and Not I. This was then cloned to the multiple cloning site of pc DNA 3.1 (+)(Zeo) (Invitrogen—Cat No: V860-20) to make the pc DNA3.1(+) (Zeo) MLS-NR2B-IRES-GFP-α-CaMKII.

HEK-293 cells were then seeded at a density of 250,000 cells per well in a six well culture plate. 48 hours later, cells were transfected with the pc DNA3.1(+) (Zeo) MLS-NR2B-IRES-GFP-α-CaMKII using lipofectamine. Twenty-four hours after transfection, cells were selected by treatment with 10% DMEM including zeocin antibiotic at 300 μg/mL After 48 hours, all the GFP expressing cells were separated out using fluorescence activated cell sorter (FACS) and maintained in medium containing the same concentration of the antibiotic. Similarly after a session of 4 FACS, spanning the period of a month, an all GFP positive cell population was obtained (MLS-2B-I-GC-Zeo-MP), (MP: denotes mixed population, I: IRES, GC: GFP-CaMKII). FIG. 21 shows transfected HEK-293 cells under zeocin selection shown through (A) bright field microscopy, (B) GFP fluorescence, and (C) an overlay of both imaging methods.

The mixed population of stable cells were trypsinised and seeded at very low density in 6-well culture plates. 24 hours later, attached single cells were marked under a light microscope. After they formed colonies, each colony of cells was aseptically transferred using colony picking method, into new wells where they multiplied and formed a homogenous population/clone of cells. They were designated as MLS-2B-I-GC-Zeo-CL-1 (Clone 1).

The clones were further checked for the specificity of calcium signal (FIG. 22). They showed calcium dependent punctae formation upon ionomycin mediated calcium influx treatment which was absent in cells where no calcium treatment was given.

What is claimed is:
1. A method of producing stable calcium sensor cell clones comprising:
   i) generating a nucleic acid sequence comprising a first nucleic acid encoding a chimeric protein and a second nucleic acid encoding either:
      a) a protein comprising amino acids 1271-1311 of rat NR2B and capable of binding to the T-site of $Ca^{2+}$/calmodulin dependent protein kinase II (CaMKII); or
      b) a fusion protein comprising amino acids 1271-1311 of rat NR2B and capable of binding to the T-site of CaMKII, conjugated to a mitochondrial localizing sequence;
      wherein the chimeric protein comprises α-CaMKII, or a mutant thereof maintaining a functioning T-site, and a fluorescent protein, and wherein the nucleic acid sequence further comprises an internal ribosome entry site (IRES) sequence between the first nucleic acid and the second nucleic acid;
   ii) generating an expression vector with a unique antibiotic selection marker expression cassette for the nucleic acid sequence mentioned in item (i) by subcloning the nucleic acid sequence mentioned in item (i) into the expression vector;

---

SEQUENCE LISTING

<160> NUMBER OF SEQ ID NOS: 4

<210> SEQ ID NO 1
<211> LENGTH: 27
<212> TYPE: DNA
<213> ORGANISM: Rattus norvegicus

<400> SEQUENCE: 1
cggggtacca tggctaccat cacctgc                                27

<210> SEQ ID NO 2
<211> LENGTH: 29
<212> TYPE: DNA
<213> ORGANISM: Rattus norvegicus

<400> SEQUENCE: 2
cgcggatccc tatcaatggg gcaggacgg                              29

<210> SEQ ID NO 3
<211> LENGTH: 23
<212> TYPE: DNA
<213> ORGANISM: Artificial Sequence
<220> FEATURE:
<223> OTHER INFORMATION: Forward primer for GFP

<400> SEQUENCE: 3
gctctagaat ggtgagcaag ggc                                    23

<210> SEQ ID NO 4
<211> LENGTH: 39
<212> TYPE: DNA
<213> ORGANISM: Artificial Sequence
<220> FEATURE:
<223> OTHER INFORMATION: reverse primer for CaMKII

<400> SEQUENCE: 4
ataagaatgc ggccgctcat caatggggca ggacggagg                   39 iii) transfecting cells with the expression vector generated as mentioned in item (ii);
iv) subjecting the cells to antibiotic selection pressure using the antibiotic referred in item (ii);
v) sorting all the cells expressing the fluorescent protein mentioned in item (i) by fluorescence activated cell sorter (FACS) technology and subjecting the sorted cells again to antibiotic selection pressure as mentioned in item (iv);
vi) repeating cycles comprising the procedures mentioned in item (iv) followed by item (v) until almost all cells are positive for the fluorescent protein; and
vii) subjecting the cells obtained in item (vi) that stably express the fluorescent protein to clonal selection by seeding the cells at low density and separating colonies formed from single cells by colony picking method and by expanding the colonies.

* * * * *